(12) United States Patent
Donegan et al.

(10) Patent No.: US 11,918,936 B2
(45) Date of Patent: Mar. 5, 2024

(54) PERFORMANCE AND DYNAMIC RANGE FOR OLIGONUCLEOTIDE BIOANALYSIS THROUGH REDUCTION OF NON SPECIFIC BINDING

(71) Applicant: Waters Technologies Corporation, Milford, MA (US)

(72) Inventors: Michael Donegan, Charlton, MA (US); Martin Gilar, Franklin, MA (US); Armand Gatien Ngounou Wetie, Seekonk, MA (US)

(73) Assignee: Waters Technologies Corporation, Milford, MA (US)

( * ) Notice: Subject to any disclaimer, the term of this patent is extended or adjusted under 35 U.S.C. 154(b) by 323 days.

(21) Appl. No.: 17/150,911

(22) Filed: Jan. 15, 2021

(65) Prior Publication Data
US 2021/0220755 A1 Jul. 22, 2021

Related U.S. Application Data

(60) Provisional application No. 63/058,737, filed on Jul. 30, 2020, provisional application No. 62/962,487, filed on Jan. 17, 2020.

(51) Int. Cl.
B01D 15/38 (2006.01)
G01N 30/34 (2006.01)

(52) U.S. Cl.
CPC ......... B01D 15/3828 (2013.01); G01N 30/34 (2013.01)

(58) Field of Classification Search
None
See application file for complete search history.

(56) References Cited

U.S. PATENT DOCUMENTS 2,801,186 A 7/1957 Alexander et al.
4,207,188 A 6/1980 Tsuda et al.
(Continued)

FOREIGN PATENT DOCUMENTS

AU 2020244497 A1 10/2020
CA 2538124 C 7/2010
(Continued)

OTHER PUBLICATIONS

Vaidya, Shyam V., et al. "Protein-resistant properties of a chemical vapor deposited alkyl-functional carboxysilane coating characterized using quartz crystal microbalance." Applied Surface Science 364 (2016): 896-908. (Year: 2016).*
(Continued)

Primary Examiner — Bradley R Spies
Assistant Examiner — Jeannie McDermott
(74) Attorney, Agent, or Firm — WOMBLE BOND DICKINSON (US) LLP; Deborah M. Vernon; Matthew J. Powers

(57) ABSTRACT

The present disclosure discusses a method of separating a sample including oligonucleotides including coating a flow path of a chromatographic system; injecting the sample comprising oligonucleotides into the chromatographic system; flowing the sample through the chromatographic system; and separating the oligonucleotides. In some examples, the coating of the flow path is non-binding with respect to the analyte, such as oligonucleotides. Consequently, the analyte does not bind to the coating of the flow path. The non-binding coating eliminates the need for passivation, which can eliminate the formerly needed time to passivate as well. In addition, analyte can be recovered with a first injection in a system, such as chromatographic system.

18 Claims, 13 Drawing Sheets
Specification includes a Sequence Listing.

(56) References Cited

U.S. PATENT DOCUMENTS

| | | |
|---|---|---|
| 4,708,782 A | 11/1987 | Andresen et al. |
| 4,711,820 A | 12/1987 | Arkles et al. |
| 4,833,093 A | 5/1989 | Malmqvist et al. |
| 4,945,282 A | 7/1990 | Kawamura et al. |
| 4,999,162 A | 3/1991 | Wells et al. |
| 5,002,794 A | 3/1991 | Ratner et al. |
| 5,153,072 A | 10/1992 | Ratner et al. |
| 5,470,463 A | 11/1995 | Girot et al. |
| 5,550,184 A | 8/1996 | Halling |
| 5,595,813 A | 1/1997 | Ogawa et al. |
| 5,643,436 A | 7/1997 | Ogawa et al. |
| 5,658,732 A | 8/1997 | Ebersole et al. |
| 5,688,855 A | 11/1997 | Stoy et al. |
| 5,856,192 A | 1/1999 | Bloch |
| 5,876,753 A | 3/1999 | Timmons et al. |
| 5,877,028 A | 3/1999 | Chandler et al. |
| 5,909,314 A | 6/1999 | Oka et al. |
| 6,013,372 A | 1/2000 | Hayakawa et al. |
| 6,054,227 A | 4/2000 | Greenberg et al. |
| 6,074,981 A | 6/2000 | Tada et al. |
| 6,121,608 A | 9/2000 | Takada et al. |
| 6,194,346 B1 | 2/2001 | Tada et al. |
| 6,207,263 B1 | 3/2001 | Takematsu et al. |
| RE37,183 E | 5/2001 | Kawamura et al. |
| 6,265,026 B1 | 7/2001 | Wang |
| 6,277,489 B1 | 8/2001 | Abbott et al. |
| 6,306,506 B1 | 10/2001 | Timmons et al. |
| 6,329,024 B1 | 12/2001 | Timmons et al. |
| 6,329,209 B1 | 12/2001 | Wagner et al. |
| 6,337,129 B1 | 1/2002 | Watanabe et al. |
| 6,340,404 B1 | 1/2002 | Oka et al. |
| 6,383,642 B1 | 5/2002 | Le Bellac et al. |
| 6,436,682 B1 | 8/2002 | Bryan et al. |
| 6,440,565 B1 | 8/2002 | Kim et al. |
| 6,444,326 B1 | 9/2002 | Smith |
| 6,461,334 B1 | 10/2002 | Buch-Rasmussen et al. |
| 6,465,056 B1 | 10/2002 | Chabrecek et al. |
| 6,482,531 B1 | 11/2002 | Timmons et al. |
| 6,547,868 B1 | 4/2003 | Belmares et al. |
| 6,599,594 B1 | 7/2003 | Walther et al. |
| 6,645,378 B1 | 11/2003 | Liu et al. |
| 6,660,338 B1 | 12/2003 | Hargreaves |
| 6,686,035 B2 | 2/2004 | Jiang et al. |
| 6,706,408 B2 | 3/2004 | Jelle |
| 6,743,516 B2 | 6/2004 | Murphy et al. |
| 6,763,437 B1 | 7/2004 | Nguyen et al. |
| 6,783,800 B2 | 8/2004 | Saito et al. |
| 6,844,028 B2 | 1/2005 | Mao et al. |
| 6,873,387 B2 | 3/2005 | Hokazono et al. |
| 6,905,772 B2 | 6/2005 | Shoup et al. |
| 6,916,541 B2 | 7/2005 | Pantano et al. |
| 6,991,826 B2 | 1/2006 | Pellerite et al. |
| 7,067,194 B2 | 6/2006 | Mao et al. |
| 7,138,186 B2 | 11/2006 | Luten, III |
| 7,250,214 B2 | 7/2007 | Walter et al. |
| 7,285,674 B2 | 10/2007 | Palma et al. |
| 7,294,365 B2 | 11/2007 | Hayakawa et al. |
| 7,351,477 B2 | 4/2008 | Yamaya et al. |
| 7,387,836 B2 | 6/2008 | Gianolio et al. |
| 7,413,774 B2 | 8/2008 | Kobrin et al. |
| 7,419,636 B2 | 9/2008 | Aker et al. |
| 7,419,699 B2 | 9/2008 | Kitada et al. |
| 7,431,969 B2 | 10/2008 | Gleason et al. |
| 7,553,514 B2 | 6/2009 | Fan et al. |
| 7,629,029 B2 | 12/2009 | Mao et al. |
| 7,638,167 B2 | 12/2009 | Kobrin et al. |
| 7,662,936 B2 | 2/2010 | Kadkhodayan et al. |
| 7,687,239 B2 | 3/2010 | Goldberg et al. |
| 7,695,775 B2 | 4/2010 | Kobrin et al. |
| 7,732,216 B2 | 6/2010 | Nochumson et al. |
| 7,736,735 B2 | 6/2010 | Kanamori et al. |
| 7,776,396 B2 | 8/2010 | Kobrin et al. |
| 7,785,649 B2 | 8/2010 | Jung et al. |
| 7,815,922 B2 | 10/2010 | Chaney et al. |
| 7,842,393 B2 | 11/2010 | Kuzuya et al. |
| 7,879,396 B2 | 2/2011 | Kobrin et al. |
| 7,901,744 B2 | 3/2011 | Denes et al. |
| 7,935,489 B2 | 5/2011 | O'Neill et al. |
| 7,935,659 B2 | 5/2011 | Nova et al. |
| 7,955,656 B2 | 6/2011 | Murayama et al. |
| 7,955,704 B2 | 6/2011 | Lowery et al. |
| 8,008,225 B2 | 8/2011 | Henze et al. |
| 8,025,915 B2 | 9/2011 | Haines et al. |
| 8,062,881 B2 | 11/2011 | Bookbinder et al. |
| 8,105,821 B2 | 1/2012 | McGall et al. |
| 8,147,954 B2 | 4/2012 | Lee et al. |
| 8,163,354 B2 | 4/2012 | Dang et al. |
| 8,178,168 B2 | 5/2012 | O'Neill et al. |
| 8,178,602 B2 | 5/2012 | Mao et al. |
| 8,323,166 B2 | 12/2012 | Haines et al. |
| 8,349,408 B2 | 1/2013 | Dulka et al. |
| 8,366,814 B2 | 2/2013 | Jones et al. |
| 8,404,621 B2 | 3/2013 | Ikeda et al. |
| 8,512,864 B2 | 8/2013 | Konno et al. |
| 8,557,748 B2 | 10/2013 | Ikeda et al. |
| 8,580,355 B2 | 11/2013 | Durandeau et al. |
| 8,652,588 B2 | 2/2014 | Teer et al. |
| 8,668,972 B2 | 3/2014 | Lewis et al. |
| 8,691,104 B2 | 4/2014 | Greer et al. |
| 8,709,588 B2 | 4/2014 | Cadet et al. |
| 8,741,158 B2 | 6/2014 | Aytug et al. |
| 8,778,278 B2 | 7/2014 | Xiong et al. |
| 8,784,565 B2 | 7/2014 | Hillabrand et al. |
| 8,795,787 B2 | 8/2014 | Jehle |
| 8,841,070 B2 | 9/2014 | Harnack et al. |
| 8,992,590 B2 | 3/2015 | Ott et al. |
| 8,993,479 B2 | 3/2015 | Zuilhof et al. |
| 9,034,660 B2 | 5/2015 | Boday et al. |
| 9,075,189 B2 | 7/2015 | West |
| 9,108,012 B2 | 8/2015 | Pryce Lewis et al. |
| 9,175,026 B2 | 11/2015 | Garrell et al. |
| 9,255,929 B2 | 2/2016 | Jiang et al. |
| 9,272,095 B2 | 3/2016 | Felts et al. |
| 9,308,520 B2 | 4/2016 | Ekeroth |
| 9,340,880 B2 | 5/2016 | Mattzela |
| 9,364,853 B2 | 6/2016 | Chen |
| 9,388,315 B2 | 7/2016 | Hoshino |
| 9,445,504 B2 | 9/2016 | Kang et al. |
| 9,475,225 B2 | 10/2016 | Giraud et al. |
| 9,523,004 B2 | 12/2016 | Hervieu et al. |
| 9,533,006 B2 | 1/2017 | Jiang et al. |
| 9,541,480 B2 | 1/2017 | Chang et al. |
| 9,556,360 B2 | 1/2017 | McGall et al. |
| 9,777,368 B2 | 10/2017 | Smith et al. |
| 9,915,001 B2 | 3/2018 | Yuan et al. |
| 9,925,521 B2 | 3/2018 | Wyndham et al. |
| 9,926,203 B2 | 3/2018 | Zhou |
| 9,975,143 B2 | 5/2018 | Smith et al. |
| 9,999,901 B2 | 6/2018 | Boscher et al. |
| 10,472,769 B2 | 11/2019 | Tuteja et al. |
| 10,604,660 B2 | 3/2020 | Smith et al. |
| 10,813,609 B2 | 10/2020 | Goto et al. |
| 10,813,610 B2 | 10/2020 | Yoshida et al. |
| 10,814,253 B2 | 10/2020 | Lipkens et al. |
| 10,814,305 B2 | 10/2020 | Liao et al. |
| 10,814,319 B2 | 10/2020 | Dasgupta et al. |
| 10,814,320 B2 | 10/2020 | Le et al. |
| 10,814,740 B2 | 10/2020 | Wilhide |
| 10,815,247 B2 | 10/2020 | Flemming et al. |
| 10,815,269 B2 | 10/2020 | Maloisel et al. |
| 10,816,115 B2 | 10/2020 | Buerger et al. |
| 10,816,476 B2 | 10/2020 | Nunney et al. |
| 10,816,487 B2 | 10/2020 | Matney et al. |
| 10,816,515 B2 | 10/2020 | Hollnagel et al. |
| 10,816,518 B2 | 10/2020 | Jarrold et al. |
| 10,816,786 B2 | 10/2020 | Douglas-Hamilton et al. |
| 10,818,485 B2 | 10/2020 | Yamaguchi |
| 10,818,486 B2 | 10/2020 | Corr et al. |
| 10,828,665 B2 | 11/2020 | Stiff-Roberts et al. |
| 10,876,202 B2 | 12/2020 | Verbeck, IV et al. |
| 10,876,210 B1 | 12/2020 | Claussen et al. |
| 10,895,009 B2 | 1/2021 | Carr et al. |
| 10,912,714 B2 | 2/2021 | Weikart et al. |
| 11,435,327 B2 | 9/2022 | Matsumoto |

(56) References Cited

U.S. PATENT DOCUMENTS

| | | |
|---|---|---|
| 11,442,064 B2 | 9/2022 | Koskinen et al. |
| 11,511,213 B2 | 11/2022 | Belanger et al. |
| 2001/0021446 A1 | 9/2001 | Takematsu et al. |
| 2002/0003109 A1 | 1/2002 | Gjerde et al. |
| 2002/0016250 A1 | 2/2002 | Hayakawa et al. |
| 2002/0020053 A1 | 2/2002 | Fonash et al. |
| 2002/0026899 A1 | 3/2002 | McLaughlin et al. |
| 2002/0142621 A1 | 10/2002 | Wang |
| 2002/0172938 A1 | 11/2002 | Cuomo et al. |
| 2002/0195950 A1 | 12/2002 | Mikhael et al. |
| 2003/0049860 A1 | 3/2003 | Cholewa |
| 2003/0057154 A1 | 3/2003 | Gjerde et al. |
| 2003/0059573 A1 | 3/2003 | Timmons et al. |
| 2003/0109062 A1 | 6/2003 | Inomata et al. |
| 2003/0113477 A1 | 6/2003 | Timmons et al. |
| 2003/0138645 A1 | 7/2003 | Gleason et al. |
| 2004/0261703 A1 | 12/2004 | Kobrin et al. |
| 2005/0118595 A1 | 6/2005 | Lahann |
| 2005/0164402 A1 | 7/2005 | Belisle et al. |
| 2005/0214803 A1 | 9/2005 | Wang |
| 2006/0073521 A1 | 4/2006 | Saito et al. |
| 2006/0110594 A1 | 5/2006 | Frutos et al. |
| 2006/0213441 A1 | 9/2006 | Kobrin et al. |
| 2006/0219598 A1 | 10/2006 | Cody et al. |
| 2006/0251795 A1 | 11/2006 | Kobrin et al. |
| 2007/0031854 A1 | 2/2007 | Katsilometes |
| 2007/0048747 A1 | 3/2007 | Leslie et al. |
| 2007/0065591 A1 | 3/2007 | Parbhu |
| 2007/0122308 A1 | 5/2007 | Ikeda et al. |
| 2007/0172666 A1 | 7/2007 | Denes et al. |
| 2007/0254378 A1 | 11/2007 | Zhang et al. |
| 2008/0041105 A1 | 2/2008 | Hahn et al. |
| 2008/0075960 A1 | 3/2008 | Pocius et al. |
| 2008/0085528 A1 | 4/2008 | Marcinkeviciene et al. |
| 2008/0170230 A1 | 7/2008 | Gerion |
| 2008/0188010 A1 | 8/2008 | Saitoh et al. |
| 2008/0248589 A1 | 10/2008 | Belisle et al. |
| 2008/0312356 A1 | 12/2008 | Kobrin et al. |
| 2009/0020712 A1 | 1/2009 | Matsumoto |
| 2009/0078633 A1 | 3/2009 | Chen et al. |
| 2009/0081371 A1 | 3/2009 | Minami et al. |
| 2009/0137526 A1 | 5/2009 | Jubert et al. |
| 2009/0162571 A1 | 6/2009 | Haines et al. |
| 2009/0176084 A1 | 7/2009 | Yoshihara et al. |
| 2009/0206034 A1 | 8/2009 | Nakajima |
| 2009/0286435 A1 | 11/2009 | Badyal et al. |
| 2009/0318609 A1 | 12/2009 | Badyal et al. |
| 2010/0038298 A1 | 2/2010 | Angelini et al. |
| 2010/0080903 A1 | 4/2010 | Tamitsuji et al. |
| 2010/0178512 A1 | 7/2010 | Giesenberg et al. |
| 2010/0196724 A1 | 8/2010 | Yamasaki et al. |
| 2010/0200207 A1 | 8/2010 | Fukuda et al. |
| 2010/0203646 A1 | 8/2010 | Larsen et al. |
| 2010/0282077 A1 | 11/2010 | Jones et al. |
| 2010/0285596 A1 | 11/2010 | Yu et al. |
| 2010/0330278 A1 | 12/2010 | Choi et al. |
| 2011/0000658 A1 | 1/2011 | Tanaka et al. |
| 2011/0062047 A1 | 3/2011 | Haines et al. |
| 2011/0120213 A1 | 5/2011 | Hirayama et al. |
| 2011/0120940 A1 | 5/2011 | Allen et al. |
| 2011/0189493 A1 | 8/2011 | Ott et al. |
| 2011/0295033 A1 | 12/2011 | Mayorga et al. |
| 2012/0069295 A1 | 3/2012 | Fukagawa et al. |
| 2012/0100546 A1 | 4/2012 | Lowery, Jr. et al. |
| 2012/0123345 A1 | 5/2012 | Felts et al. |
| 2012/0132794 A1 | 5/2012 | Buchanan et al. |
| 2012/0178848 A1 | 7/2012 | Adkinson et al. |
| 2012/0219697 A1 | 8/2012 | Chen |
| 2012/0219727 A1 | 8/2012 | Gandhiraman et al. |
| 2012/0251797 A1 | 10/2012 | Smith et al. |
| 2012/0252709 A1 | 10/2012 | Felts et al. |
| 2012/0288717 A1 | 11/2012 | Mao et al. |
| 2013/0004780 A1 | 1/2013 | Hervieu et al. |
| 2013/0025503 A1 | 1/2013 | Park et al. |
| 2013/0029138 A1 | 1/2013 | Benard et al. |
| 2013/0090260 A1 | 4/2013 | Nova et al. |
| 2013/0136937 A1 | 5/2013 | Fujii et al. |
| 2013/0157062 A1 | 6/2013 | Kihara et al. |
| 2013/0174642 A1 | 7/2013 | Bourlon et al. |
| 2013/0244025 A1 | 9/2013 | Smith et al. |
| 2013/0266762 A1 | 10/2013 | Mayers et al. |
| 2013/0337226 A1 | 12/2013 | Curran et al. |
| 2014/0004022 A1 | 1/2014 | Sagona et al. |
| 2014/0065368 A1 | 3/2014 | Aytug et al. |
| 2014/0147631 A1 | 5/2014 | Yang et al. |
| 2014/0154399 A1 | 6/2014 | Weikart et al. |
| 2014/0187666 A1 | 7/2014 | Aizenberg et al. |
| 2014/0202355 A1 | 7/2014 | Hoshino |
| 2014/0273080 A1* | 9/2014 | Apffel, Jr. .......... G01N 33/5005 435/40.5 |
| 2014/0287240 A1 | 9/2014 | Murotani et al. |
| 2014/0299538 A1 | 10/2014 | Gleason et al. |
| 2014/0318748 A1 | 10/2014 | Svensson et al. |
| 2014/0323981 A1 | 10/2014 | Giraud et al. |
| 2014/0342954 A1 | 11/2014 | Ingber et al. |
| 2014/0357091 A1 | 12/2014 | Mattzela |
| 2014/0370300 A1 | 12/2014 | Smith |
| 2015/0021339 A1 | 1/2015 | Felts et al. |
| 2015/0024152 A1* | 1/2015 | Carr ...................... C23C 16/401 428/34.1 |
| 2015/0030885 A1 | 1/2015 | Smith |
| 2015/0064376 A1 | 3/2015 | Smith et al. |
| 2015/0064451 A1 | 3/2015 | Kalaga et al. |
| 2015/0098084 A1 | 4/2015 | Felts et al. |
| 2015/0118502 A1 | 4/2015 | Mitsuhashi et al. |
| 2015/0118504 A1 | 4/2015 | Ohshita et al. |
| 2015/0122365 A1 | 5/2015 | Carr et al. |
| 2015/0152124 A1 | 6/2015 | Mori et al. |
| 2015/0175814 A1 | 6/2015 | Aizenberg et al. |
| 2015/0209846 A1 | 7/2015 | Aizenberg et al. |
| 2015/0210951 A1 | 7/2015 | Aizenberg et al. |
| 2015/0232806 A1 | 8/2015 | Jung et al. |
| 2015/0239773 A1 | 8/2015 | Aytug |
| 2015/0247051 A1 | 9/2015 | Ha et al. |
| 2015/0273522 A1 | 10/2015 | Boscher et al. |
| 2015/0283307 A1 | 10/2015 | Smith et al. |
| 2015/0298165 A1 | 10/2015 | Smith |
| 2015/0307525 A1 | 10/2015 | Higano et al. |
| 2015/0307719 A1 | 10/2015 | Mitsuhashi et al. |
| 2015/0309216 A1 | 10/2015 | Fournand |
| 2015/0322272 A1 | 11/2015 | Pokroy et al. |
| 2015/0329725 A1 | 11/2015 | Liu |
| 2016/0002488 A1 | 1/2016 | Takao et al. |
| 2016/0002489 A1 | 1/2016 | Gleason et al. |
| 2016/0017397 A1 | 1/2016 | Roy et al. |
| 2016/0038972 A1 | 2/2016 | Lu |
| 2016/0040039 A1 | 2/2016 | Yamane et al. |
| 2016/0059260 A1 | 3/2016 | Smith et al. |
| 2016/0074862 A1 | 3/2016 | Breaux et al. |
| 2016/0168021 A1 | 6/2016 | Goh et al. |
| 2016/0200941 A1 | 7/2016 | Liu et al. |
| 2016/0231594 A1 | 8/2016 | Ang et al. |
| 2016/0243308 A1 | 8/2016 | Giraud et al. |
| 2016/0251261 A1 | 9/2016 | Bureau |
| 2016/0289824 A1 | 10/2016 | Mattzela et al. |
| 2016/0302723 A1 | 10/2016 | Chen |
| 2016/0340544 A1 | 11/2016 | Katsukawa et al. |
| 2017/0001956 A1 | 1/2017 | Chau et al. |
| 2017/0044315 A1 | 2/2017 | Mitsuhashi et al. |
| 2017/0173223 A1 | 6/2017 | Delaney, Jr. et al. |
| 2018/0049644 A1 | 2/2018 | Themelis |
| 2018/0258529 A1* | 9/2018 | Vezza .................... C23C 16/24 |
| 2018/0357402 A1 | 12/2018 | Omata et al. |
| 2019/0032201 A1 | 1/2019 | Smith et al. |
| 2019/0077966 A1 | 3/2019 | Koguchi et al. |
| 2019/0086371 A1* | 3/2019 | Lauber .................... C23C 14/12 |
| 2019/0170705 A1 | 6/2019 | Wyndham .............. G01N 30/50 |
| 2019/0271711 A1 | 9/2019 | Egan et al. |
| 2019/0292220 A1* | 9/2019 | Birdsall .............. G01N 33/6848 |
| 2019/0390329 A1 | 12/2019 | Carr et al. |
| 2020/0024155 A1 | 1/2020 | Kano et al. |
| 2020/0024156 A1 | 1/2020 | Kano et al. |
| 2020/0024157 A1 | 1/2020 | Kano et al. |
| 2020/0025729 A1 | 1/2020 | Milburn et al. |

(56) References Cited

U.S. PATENT DOCUMENTS

| | | |
|---|---|---|
| 2020/0062615 A1 | 2/2020 | Rajagopalan et al. |
| 2020/0109297 A1 | 4/2020 | McDaniel |
| 2020/0189938 A1 | 6/2020 | Kano et al. |
| 2020/0215457 A1 | 7/2020 | DeLano et al. |
| 2020/0239641 A1 | 7/2020 | Kawakami et al. |
| 2020/0328073 A1 | 10/2020 | Peterson et al. |
| 2020/0332801 A1 | 10/2020 | Kimura |
| 2020/0333265 A1 | 10/2020 | Doki et al. |
| 2020/0333369 A1 | 10/2020 | Toyoda et al. |
| 2020/0334792 A1 | 10/2020 | Themelis |
| 2020/0335902 A1 | 10/2020 | Tanaka |
| 2020/0337659 A1 | 10/2020 | Sano et al. |
| 2020/0338528 A1 | 10/2020 | Dong et al. |
| 2020/0339322 A1 | 10/2020 | Christensen et al. |
| 2020/0339665 A1 | 10/2020 | Bruhlmann et al. |
| 2020/0339931 A1 | 10/2020 | Bremer et al. |
| 2020/0339977 A1 | 10/2020 | Lebofsky et al. |
| 2020/0339980 A1 | 10/2020 | Dellinger et al. |
| 2020/0340047 A1 | 10/2020 | Mollerup |
| 2020/0340468 A1 | 10/2020 | Kuntz et al. |
| 2020/0340889 A1 | 10/2020 | Mlcak et al. |
| 2020/0340890 A1 | 10/2020 | Mlcak |
| 2020/0340910 A1 | 10/2020 | Handique |
| 2020/0340946 A1 | 10/2020 | Bateman et al. |
| 2020/0340949 A1 | 10/2020 | Mlcak et al. |
| 2020/0340950 A1 | 10/2020 | Mlcak et al. |
| 2020/0340956 A1 | 10/2020 | Ortmann et al. |
| 2020/0340959 A1 | 10/2020 | Schultz et al. |
| 2020/0340961 A1 | 10/2020 | Kunimura |
| 2020/0340982 A1 | 10/2020 | Levin et al. |
| 2020/0341253 A1 | 10/2020 | Foelling |
| 2020/0341255 A1 | 10/2020 | Chan |
| 2020/0341259 A1 | 10/2020 | Chan et al. |
| 2020/0341278 A1 | 10/2020 | Tanaka |
| 2020/0341378 A1 | 10/2020 | Wolterink et al. |
| 2020/0342326 A1 | 10/2020 | Rahnama Moghaddam |
| 2020/0342672 A1 | 10/2020 | Schmelig et al. |
| 2020/0343082 A1 | 10/2020 | Richardson et al. |
| 2020/0348307 A1 | 11/2020 | Beierle et al. |
| 2020/0365237 A1 | 11/2020 | Madden et al. |
| 2020/0375846 A1 | 12/2020 | Chang et al. |
| 2021/0009817 A1 | 1/2021 | Poulet et al. |
| 2021/0009883 A1 | 1/2021 | Tuteja et al. |
| 2021/0032157 A1 | 2/2021 | Czihal et al. |
| 2021/0061049 A1 | 3/2021 | Lekon et al. |
| 2021/0098233 A1 | 4/2021 | Kapoor et al. |
| 2021/0101176 A1 | 4/2021 | Baltazar et al. |
| 2021/0108252 A1 | 4/2021 | Beverly |
| 2021/0255196 A1* | 8/2021 | Birdsall ............ G01N 30/7233 |

FOREIGN PATENT DOCUMENTS

| | | |
|---|---|---|
| CA | 2881275 C | 10/2020 |
| CA | 2855353 C | 1/2021 |
| CN | 104327663 A | 2/2015 |
| CN | 109225113 A | 1/2019 |
| CN | 109608680 A | 4/2019 |
| CN | 111471977 A | 7/2020 |
| CN | 111560172 A | 8/2020 |
| CN | 111848755 A | 10/2020 |
| CN | 111855826 A | 10/2020 |
| CN | 111855827 A | 10/2020 |
| CN | 111863585 A | 10/2020 |
| CN | 111944153 A | 11/2020 |
| CN | 112011055 A | 12/2020 |
| CN | 112264272 A | 1/2021 |
| EP | 1816155 B1 | 6/2011 |
| EP | 2587258 A1 | 5/2013 |
| EP | 2608219 B1 | 3/2015 |
| EP | 2915833 A1 | 9/2015 |
| EP | 3573646 A1 | 12/2019 |
| EP | 3633366 A1 | 4/2020 |
| EP | 2403621 B1 | 10/2020 |
| EP | 2798664 B1 | 10/2020 |
| EP | 2834837 B1 | 10/2020 |
| EP | 2900819 B1 | 10/2020 |
| EP | 3006980 B1 | 10/2020 |
| EP | 3060325 B1 | 10/2020 |
| EP | 3131657 B1 | 10/2020 |
| EP | 3139150 B1 | 10/2020 |
| EP | 3169232 B1 | 10/2020 |
| EP | 3169424 B1 | 10/2020 |
| EP | 3273674 B1 | 10/2020 |
| EP | 3344317 B1 | 10/2020 |
| EP | 3399074 B1 | 10/2020 |
| EP | 3545085 A4 | 10/2020 |
| EP | 3727152 A1 | 10/2020 |
| EP | 3727637 A1 | 10/2020 |
| EP | 3727679 A1 | 10/2020 |
| EP | 3727690 A1 | 10/2020 |
| EP | 3728046 A1 | 10/2020 |
| EP | 3728581 A1 | 10/2020 |
| EP | 3728621 A2 | 10/2020 |
| EP | 3728633 A1 | 10/2020 |
| EP | 3729055 A1 | 10/2020 |
| EP | 3729071 A1 | 10/2020 |
| EP | 3729077 A1 | 10/2020 |
| EP | 3729083 A1 | 10/2020 |
| EP | 3729162 A1 | 10/2020 |
| EP | 3729487 A1 | 10/2020 |
| EP | 3729488 A2 | 10/2020 |
| EP | 3730119 A1 | 10/2020 |
| EP | 3730324 A1 | 10/2020 |
| EP | 3730406 A1 | 10/2020 |
| EP | 3730538 A1 | 10/2020 |
| EP | 3730599 A1 | 10/2020 |
| EP | 3730922 A1 | 10/2020 |
| EP | 3730923 A1 | 10/2020 |
| EP | 3730927 A1 | 10/2020 |
| EP | 3731393 A1 | 10/2020 |
| EP | 3749719 A1 | 12/2020 |
| EP | 3788181 A1 | 3/2021 |
| FR | 3095337 A1 | 10/2020 |
| GB | 2108403 A | 5/1983 |
| GB | 2429428 A | 2/2007 |
| GB | 2481687 A | 1/2012 |
| GB | 2490243 A | 10/2012 |
| GB | 2501803 A | 11/2013 |
| GB | 2531126 A | 4/2016 |
| GB | 2549248 A | 10/2017 |
| GB | 2534477 B | 10/2020 |
| GB | 2574723 B | 10/2020 |
| IL | 174122 A | 9/2011 |
| IL | 239213 A | 3/2020 |
| IL | 253518 A | 6/2020 |
| IL | 262854 A | 6/2020 |
| JP | 2012232870 A | 11/2012 |
| JP | 2020507460 A | 3/2020 |
| JP | 2020507462 A | 3/2020 |
| JP | 2020507466 A | 3/2020 |
| JP | 2020510522 A | 4/2020 |
| JP | 6770727 B2 | 10/2020 |
| JP | 6771390 B2 | 10/2020 |
| JP | 6771801 B2 | 10/2020 |
| JP | 6772721 B2 | 10/2020 |
| JP | 6772764 B2 | 10/2020 |
| JP | 6772953 B2 | 10/2020 |
| JP | 6773138 B2 | 10/2020 |
| JP | 6773236 B2 | 10/2020 |
| JP | 2020169857 A | 10/2020 |
| JP | 2020171429 A | 10/2020 |
| JP | 2020171482 A | 10/2020 |
| JP | 2020171483 A | 10/2020 |
| JP | 2020171484 A | 10/2020 |
| JP | 2020171882 A | 10/2020 |
| JP | 2020172518 A | 10/2020 |
| JP | 2020172703 A | 10/2020 |
| JP | 2020173192 A | 10/2020 |
| JP | 2020173427 A | 10/2020 |
| JP | 2020176195 A | 10/2020 |
| JP | 2020177669 A | 10/2020 |
| JP | 2020530329 A | 10/2020 |
| JP | 2020530909 A | 10/2020 |
| JP | 2020536764 A | 12/2020 |

(56) References Cited

FOREIGN PATENT DOCUMENTS

| | | |
|---|---|---|
| KR | 960007179 B1 | 5/1996 |
| KR | 20000019936 A | 4/2000 |
| KR | 20060130959 A | 12/2006 |
| KR | 20080071942 A | 8/2008 |
| KR | 20090103323 A | 10/2009 |
| KR | 20120007817 A | 1/2012 |
| KR | 20130020869 A | 3/2013 |
| KR | 20140082838 A | 7/2014 |
| KR | 101711786 B1 | 3/2017 |
| KR | 20170021957 A | 3/2017 |
| KR | 101742683 B1 | 6/2017 |
| KR | 20180008427 A | 1/2018 |
| KR | 20200139842 A | 12/2020 |
| KR | 20210008523 A | 1/2021 |
| KR | 102218186 B1 | 2/2021 |
| KR | 20210013582 A | 2/2021 |
| TW | 202031738 A | 9/2020 |
| TW | 202039644 A | 11/2020 |
| WO | 199119982 A1 | 12/1991 |
| WO | 1998017407 A1 | 4/1998 |
| WO | 1999040038 A1 | 8/1999 |
| WO | 199951773 A1 | 10/1999 |
| WO | 200032044 A1 | 6/2000 |
| WO | 200168240 A2 | 9/2001 |
| WO | 2002085250 A2 | 10/2002 |
| WO | 2002085330 A1 | 10/2002 |
| WO | 2003104394 A2 | 12/2003 |
| WO | 2006015982 A2 | 2/2006 |
| WO | 2006121295 A1 | 11/2006 |
| WO | 2007081387 A1 | 7/2007 |
| WO | 2007117191 A1 | 10/2007 |
| WO | 2007117213 A1 | 10/2007 |
| WO | 2007117214 A1 | 10/2007 |
| WO | 2009007150 A2 | 1/2009 |
| WO | 2010009311 A1 | 1/2010 |
| WO | 2010135660 A2 | 11/2010 |
| WO | 2012170549 A1 | 12/2012 |
| WO | 2013064754 A1 | 5/2013 |
| WO | 2014104495 A1 | 7/2014 |
| WO | 2014104573 A1 | 7/2014 |
| WO | 2014164928 A1 | 10/2014 |
| WO | 2015050449 A2 | 4/2015 |
| WO | 2015054652 A2 | 4/2015 |
| WO | 2015134488 A1 | 9/2015 |
| WO | 2016100923 A1 | 6/2016 |
| WO | 2016114850 A1 | 7/2016 |
| WO | 2016125272 A1 | 8/2016 |
| WO | 2016160702 A1 | 10/2016 |
| WO | 2016166816 A1 | 10/2016 |
| WO | 2017040623 A1 | 3/2017 |
| WO | 2017053891 A1 | 3/2017 |
| WO | 2017060991 A1 | 4/2017 |
| WO | 2017072893 A1 | 5/2017 |
| WO | 2017087032 A1 | 5/2017 |
| WO | 2017098758 A1 | 6/2017 |
| WO | 2017143246 A1 | 8/2017 |
| WO | 2017171546 A1 | 10/2017 |
| WO | 2017189357 A2 | 11/2017 |
| WO | 2017210223 A1 | 12/2017 |
| WO | 2018072862 A1 | 4/2018 |
| WO | 2018146318 A1 | 8/2018 |
| WO | 2018202935 A1 | 11/2018 |
| WO | 2019053693 A1 | 3/2019 |
| WO | 2019063482 A1 | 4/2019 |
| WO | 2019101980 A1 | 5/2019 |
| WO | 2019116619 A1 | 6/2019 |
| WO | 2019122100 A1 | 6/2019 |
| WO | 2019126130 A1 | 6/2019 |
| WO | 2019130536 A1 | 7/2019 |
| WO | 2019138705 A1 | 7/2019 |
| WO | 2019150573 A1 | 8/2019 |
| WO | 2019152724 A1 | 8/2019 |
| WO | 2019154758 A1 | 8/2019 |
| WO | 2019155543 A1 | 8/2019 |
| WO | 2019155545 A1 | 8/2019 |
| WO | 2019165297 A1 | 8/2019 |
| WO | 2019168989 A1 | 9/2019 |
| WO | 2019171085 A1 | 9/2019 |
| WO | 2019175441 A1 | 9/2019 |
| WO | 2019176081 A1 | 9/2019 |
| WO | 2019180045 A1 | 9/2019 |
| WO | 2019185607 A1 | 10/2019 |
| WO | 2019186999 A1 | 10/2019 |
| WO | 2019191269 A1 | 10/2019 |
| WO | 2019191587 A2 | 10/2019 |
| WO | 2019193558 A1 | 10/2019 |
| WO | 2019198280 A1 | 10/2019 |
| WO | 2019200306 A1 | 10/2019 |
| WO | 2019212799 A1 | 11/2019 |
| WO | 2019218088 A1 | 11/2019 |
| WO | 2019224201 A1 | 11/2019 |
| WO | 2019224540 A1 | 11/2019 |
| WO | 2019229171 A1 | 12/2019 |
| WO | 2019238469 A1 | 12/2019 |
| WO | 2019241394 A1 | 12/2019 |
| WO | 2020068174 A2 | 4/2020 |
| WO | 2020095566 A1 | 5/2020 |
| WO | 2020104521 A2 | 5/2020 |
| WO | 2020174402 A1 | 9/2020 |
| WO | 2020213061 A1 | 10/2020 |
| WO | 2020213101 A1 | 10/2020 |
| WO | 2020213209 A1 | 10/2020 |
| WO | 2020216966 A1 | 10/2020 |
| WO | 2020219451 A1 | 10/2020 |
| WO | 2020219605 A1 | 10/2020 |
| WO | 2020219659 A1 | 10/2020 |
| WO | 2020219667 A1 | 10/2020 |
| WO | 2020219671 A1 | 10/2020 |
| WO | 2020219784 A1 | 10/2020 |
| WO | 2020219869 A1 | 10/2020 |
| WO | 2021019220 A1 | 2/2021 |
| WO | 2021061049 A1 | 4/2021 |
| WO | 2021072245 A1 | 4/2021 |

OTHER PUBLICATIONS

Biba. "Chromatographic Analysis and Separation of Short RNA Oligonucleotides with Novel Liquid Chromatography Methods." Drexel University Thesis, Doctor of Philosophy. Jun. 2014.
International Search Report and Written Opinion issued in International Application No. PCT/IB2021/050315 dated Apr. 23, 2021.
Sinha et al. "Analysis and Purification of Synthetic Nucleic Acids Using HPLC." Curr. Protoc. Nucleic Acid Chem. (2015). 61: 10.5.1-10.5.39.
"High Purity Coatings, the Secret Weapon in Semiconductor Manufacturing." SilcoTek, Dec. 12, 2014.
"How to Identify and Prevent Fouling (HPL)". SilcoTek. Jun. 22, 2017.
"Solving Surface Fouling with New Non-Stick CVD Coatings." SilcoTek. Aug. 31, 2017.
"Specialty Coatings." https://geniefilters.com/news-room/specialty-coatings. Dec. 29, 2013.
"Visit US at Pittcon: Make Your HPLC System Faster & More Reliable." SilcoTek. Mar. 3, 2017.
"What's SilcoTek Talking About at Pittcon 2018." SilcoTek. Feb. 16, 2018.
Electrical Property Characterization of SilcoTek Coatings.' Retrieved on Jul. 31, 2023.
Al-Hamarneh et al. "Synthesis and characterization of di(ethylene glycol) vinyl ether films deposited by atmospheric pressure corona discharge plasma." Surface Coatings Technol. 234(2013):33-41.
Barone et al. "Characterizing the Performance of Surface Modifications that Enhance Sensitivty, Reliability, Reproducibility and Accuracy of Analytical Instruments." (2011).
Barone et al. "Improving Reliability of Analytical and Sampling Systems in Challenges and Corrosive Environments." (2011).
Beigbeder et al. "Marine Fouling Release Silicone/Carbon Nanotube Nanocomposite Coatings: On the Importance of the Nanotube Dispersion State." J. Nanosci. Nanotech, 10(2010): 2972-2978.
BIOCYL™ X1, Dec. 20, 2018.

(56) References Cited

OTHER PUBLICATIONS

Bischof. "Achieving PEEK-like Performance on Stainless Steel HPLC Components with Bio-Inert CVD Coatings." SilcoTek. Feb. 28, 2019.
Brown et al. "Sampling of gaseous sulfur-containing compounds at low concentrations with a review of best-practice methods for biogas and natural gas applications." Trends Anal. Chem. 64(2015): 42-52.
Buchmeiser. "New synthetic ways for the preparation of high-performance liquid chromatography supports." J. Chromatogr. A. 918(2001): 233-266.
Carretier et al. "Design of PVDF/PEGMA-b-PS-b-PEGMA membranes by VIPS for improved biofouling mitigation." J. Membrane Sci. 510(2016):355-369.
Cheong. "Fritting techniques in chromatography." J. Sep. Sci. 37(2014): 603-617.
Colic et al. "Synergistic Application of Chemical and Electromagnetic Water Treatment in Corrosion and Scale Prevention." Croatiia Chem. Acta. 71.4(1998): 905-916.
Conroy. "Nanostructed surfaces for sening heavy metals and radionuclides in aqueous systems." Doctorate thesis—Philosophy—The University of Leeds. Oct. 2012.
Dursan: An Inert and Corrosion Resistant High Performance CVD Coating. SilcoTek. Retrieved on Jul. 31, 2023.
Dursan® and SilcoNert® 2000 Coating Comparison Guide. (2000).
Dursan® Coating Data Sheet. Jun. 1, 2021.
Dursan® Coating for Improved, Metal-Free Liquid Chromatography. Dec. 20, 2018.
Dursan® Data Sheet 2018.
Hayes et al. "Core-shell particles: Preparation fundamentals and applications in high performance liquid chromatography." J. Chromatogr. A. 1357(2014): 36-52.
HPLC Hardware. Möller Medical. (2007).
Hsieh et al. "Effective Enhancement of Fluorescence Detection Efficiency in Protein Microarray Assays: Application of a Highly Fluorinated Organosilane as the Blocking Agent on the Background Surface by a Facile Vapor-Phase Deposition Process." Anal. Chem. 81(2009): 7908-7916.
International Search Report and Written Opinion issued in International Application No. PCT/IB2021/059534 dated Mar. 10, 2022.
Kaliaraj et al. "Bio-inspired YSZ coated titanium by EB-PVD for biomedical applications." Surface and Coatings Technol. 307(2016): 227-235.
Kanavarioti et al. "HPLC methods for purity evaluation of man-made single-stranded RNAs." Nature. 9(2019): 1019.
Kong. "Measuring the Electrostatic Repulsion Forces Beween Glycosaminoglycans Using the Atomic Force Microscope." Masters Thesis—Department of Materials Science Engineering at Massachusetts Institute of Technology, Sep. 1999.
Lauber et al. "Rapid Preparation of Released N-Glycans for HILIC Analysis Using a Labeling Reagent that Facilitates Sensitive Fluorescence and ESI-MS Detection." Anal Chem. 87.10(2015): 5401-9.
Lecloux et al. "The safe use of carbon nanotubes in coating applications." OECD Conference on Benefits of nanomaterials. Paris, Jul. 15-17, 2009.
NanoCoatings Product Information. Möller Medical. (2010).
Paleologos et al. "Micelle-mediated separation and cloud-point extraction." Trends Anal. Chem. 24.5(2005): 426-436.
Pfaunmiller et al. "Affinity monolith chromatography: A review of principles and recent analytical applications." Anal. Bionanal. Chem. 405.7(2013): 2133-2145.
Pirok et al. "Pratical Approaches to Overcome the Challenges of Comprehensive Two-Dimensional Liquid Chromatography." LCGC Europe. 31.5(2018): 242-249.
Pirok et al. "Recent Developments in Two-Dimensional Liquid Chromatography: Fundamental Improvements for Practical Applications." Anal. Chem. 91.1(2019): 240-263.
Rahimi et al. "Application of copolymer coated frits for solid-phase extraction of poly cyclic aromatic hydrocarbons in water samples." Anal. Chim. Acta. 836(2014): 45-52.
Rivera et al. "Bioinert Versus Biocompatible: The Benefits of Different Column Materials in Liquid Chromatography Separations." LCGC Suppl. 36.6(2018).
Rosmaninho et al. "Modified stainless steel surfaces targeted to reduce fouling—Evaluation of fouling by milk components." J. Food Engineering. 80(2007): 1176-1187.
Shih et al. "Silanization of Stainless-Steel Frits for Use in Trace Metal Analysis by High Performance Liquid Chromatography." Talanta. 28(1981): 411-414.
SilcoTek Coating Properties: A Comprehensive Analysis of Coating Characteristics and Properties. e-book. Retrieved 2023.
SilcoTek Intellectual Property, Patents and Trademarks. Retrieved Jul. 31, 2023.
SilcoTek® Non-Stick CVD Coatings,. Retrieved Jul. 31, 2023.
Sun et al. "Vapor-based Grafting of Crosslinked Poly(N-vinyl pyrrolidone) Coatings with Tuned Hydrophilicity and Anti-Biofouling Properties." J. Mater. Chem. B. 4(2016): 2669-2678.
Technical Program, Agenda of Sessions: Abstract PDF. Pittcon, Atlanta, GA, Mar. 6-10, 2016.
Vaidya et al. "Protein-Resistant Properties of SilcoTek's Dursan® Coating." SilcoTek. (2017).
Velox Plus, Dec. 20, 2018.
Wyndham et al. "Characterization and Evaluation of C18 HPLC Stationary Phases Based on Ethyl-Bridged Hybrid Organic/Inorganic Particles." Anal. Chem. 75.24(2003): 6781-6788.
Xue et al. "Surface-modified anodic aluminum oxide membrane with hydroxyethyl celluloses as a matrix for bilirubin removal." J. Chromatog. B. 912(2013):1-7.
Yang et al. "Synergistic Prevention of Biofouling in Seawater Desalination by Zwitterionic Surfaces and Low-Level Chloronation." Adv. Mater. 26(2014):1711-1718.
"Carboxy-silane triol." PubChem, Aug. 12, 2023.
"Corrosion Resistant Coating Properties: Extend Product Life, Prevent Contamination." SilcoTek. 2023.
"How Corrosion Resistant Is Dursan? Let's Find Out." SilcoTek. Jan. 23, 2025.
'Reliable Sampling & Transfer of Sulfur Passivation vs. Inert Coatings.' SilcoTek. Jun. 16, 2011.
"Silane Coupling Agents: Connecting Acorss Boundaries." Gelest, Inc. 2014.
Barone. "Corrosion Control and Chemically inert nano-coatings for use in refining, petrochemical and analytical equipment industries." 2021.
Barone. "Exciting Developments in Silicon Barrier Coatings for Semicon." SllcokTek. Jul. 15, 2015.
Dursan® Coating Data Sheet. 2022.
Gosetti et al. "Signal suppression/enhancement in high-performance liquid chromatography tandem mass spectrometry." J. Chromatogr. A. 1217(2010): 3929-3937.
Ntrouka et al. "The effect of chemotherapeutic agents on contaminated titanium surfaces: a systematic review." Clin. Oral Impl. Res. 22(2011): 681-690.
Waters Quality Parts®, Chromatography Columns and Supplies Catalog. Dec. 2014.

* cited by examiner

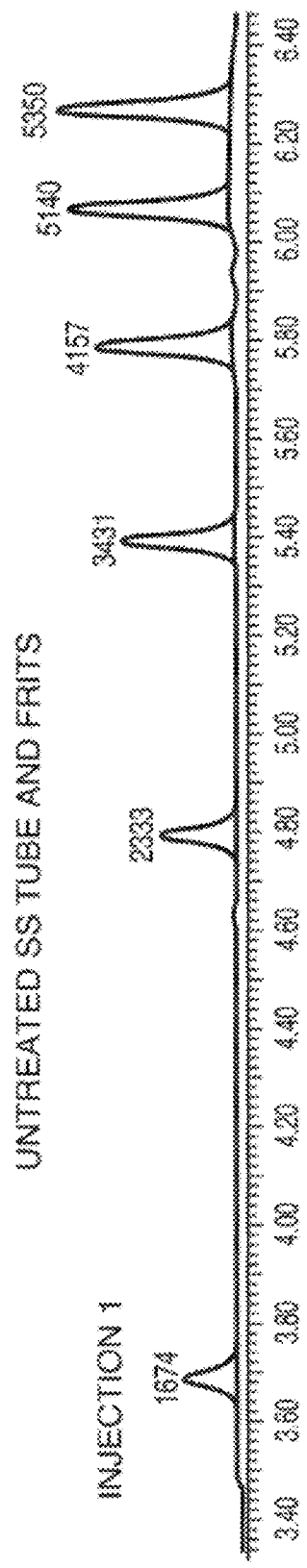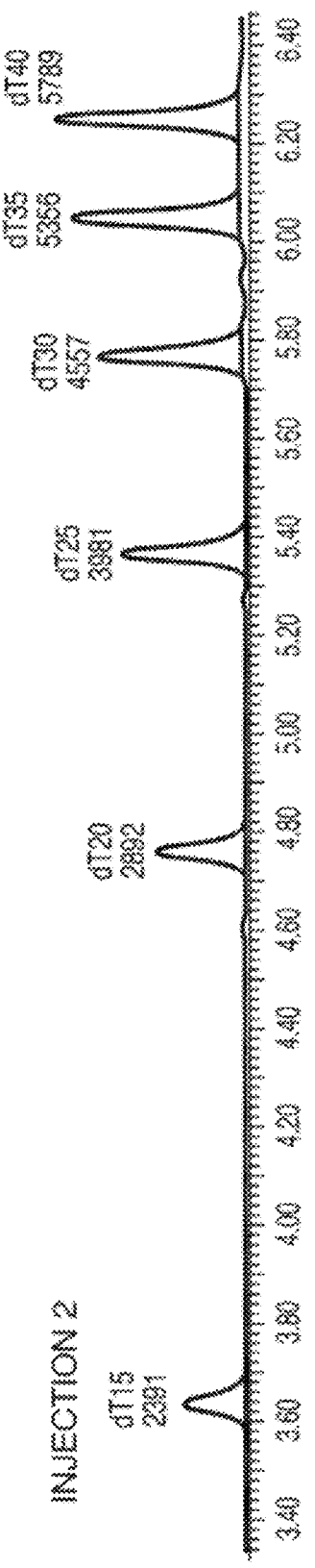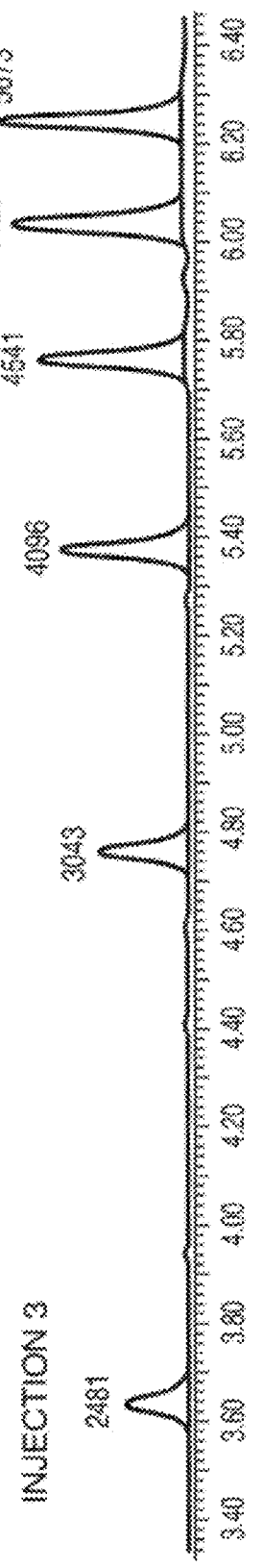

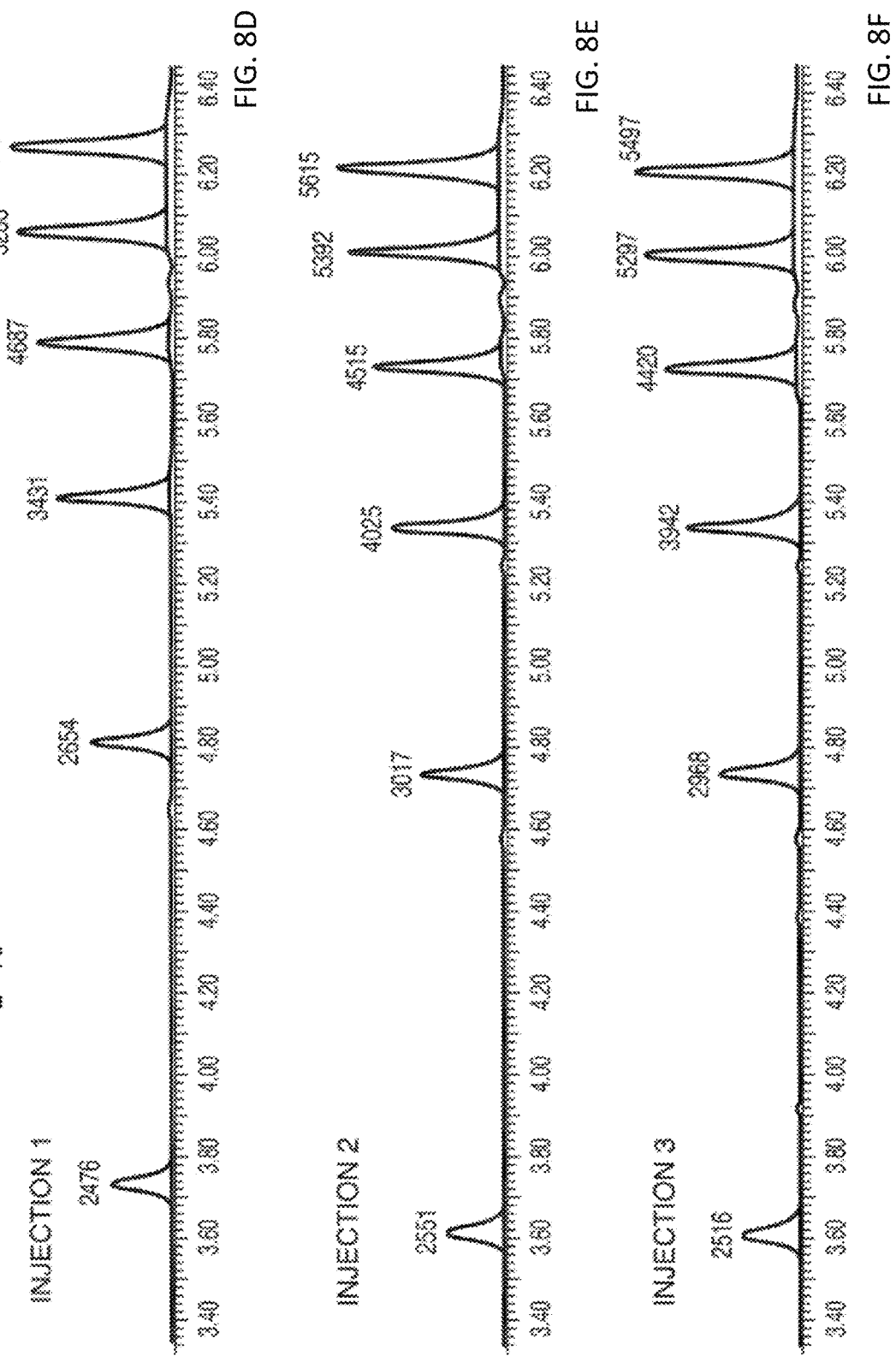

Standard Column

Standard Column

PERFORMANCE AND DYNAMIC RANGE FOR OLIGONUCLEOTIDE BIOANALYSIS THROUGH REDUCTION OF NON SPECIFIC BINDING

CROSS-REFERENCE TO RELATED APPLICATIONS

This application claims priority to U.S. Provisional Application No. 62/962,487 filed on Jan. 17, 2020 and U.S. Provisional Application No. 63/058,737 filed on Jul. 30, 2020, the contents of each are incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 13, 2021, is named W-4192-US03_SL.txt and is 2,337 bytes in size.

FIELD OF THE TECHNOLOGY

The present disclosure relates to the improved performance and dynamic range for analyzing compounds through reduction of non-specific binding. More specifically, the present disclosure relates to the use of a coating to reduce non-specific binding in chromatographic systems to improve performance, e.g., limit of detection, initial performance, and linear dynamic range, for oligonucleotide bioanalysis.

BACKGROUND

Oligonucleotides are polymeric sequences of nucleotides (RNA, DNA, and their analogs) that are utilized extensively as PCR (polymerase chain reaction) and microarray-based reagents in life science research and DNA-based diagnostic test kits (as primer and probe reagents). With increased frequency, they are being developed as therapeutic drugs for a wide range of disease conditions. Only a few FDA-approved oligonucleotide-based therapeutic drugs are on the market today, but there are over 100 currently in the clinical pipeline and many more in earlier stages of development.

Oligonucleotides developed as therapeutics can take a variety of forms, from antisense oligonucleotides (ASOs), small interfering RNAs (siRNA), small hairpin RNAs (shRNAs), and micro RNAs (miRNAs) that can effect "gene silencing," which is down-regulating or turning off the expression of specific genes/proteins; to Aptamers that behave like small molecule drugs and bind to specific disease targets; to messenger RNAs (mRNAs) that can be very long, and are being designed to up-regulate expression of a particular protein. To enhance their stability and/or cellular uptake in-vivo, oligonucleotide therapeutics often incorporate chemically-modified nucleotides, are PEGylated, or are otherwise conjugated to other chemical moieties. And like other biologics, the biophysical characteristics and purity of these molecules must be precisely understood and controlled to meet regulatory requirements.

Oligonucleotides are produced through an automated solid-phase synthesis process. Typical lengths range from 20 to 80 nucleotides (mRNAs being an exception, as they can be 1,500 or more nucleotides long). Depending on the application, synthesis scales can vary from nanograms to kilograms. While the synthesis process is efficient, it invariably results in truncated sequences and other process-related by-products/impurities that need to be separated and removed in order to meet purity requirements.

However, due to their polyanionic nature, oligonucleotides are very sticky. They tend to adhere to metallic system components in the fluidic chromatographic path such as preheaters, frits, and column bodies. This can lead to variable recoveries of oligonucleotides.

SUMMARY

Non-specific binding of oligonucleotides within chromatographic systems negatively impacts the ability to detect and accurately quantify these molecules. The mechanism of non-specific binding is due to the interaction of the analyte with metallic surfaces in the flow path. Due to the presence of multiple phosphate groups, oligonucleotides are excellent polydentate ligands capable of high affinity metal chelation. This interaction leads to a reduced amount of analyte detected, reduced repeatability of analysis, and inaccurate quantitation. This becomes especially pronounced at lower concentrations where the percentage of analyte that is bound to the surface is very high relative to the total concentration. The impact of performance claims from the analytical methods, such as limit of detection, calibration curve linearity, speed to result, robustness of analysis, and linear dynamic range, are compromised due to this unwanted interaction.

Existing techniques to mitigate these interactions, such as system passivation with nitric acid, are time consuming and only produce temporary performance gains. It is difficult to determine when the system is fully passivated and ready to operate. If attempts are made to obtain data for quantitative studies before full passivation is reached, the lower end of the curve would not be detected because the analyte still has metallic surfaces it can bind to. In order to fully address losses in both linear dynamic range and sensitivity at the lower range of detection, a more permanent solution needs to be implemented. In the present technology, coating of the metallic surfaces defining the flow path offers a pre-passivated system that has demonstrably better limit of detection and initial performance over uncoated systems.

For example, an alkylsilyl coating on the surface area defining the flow path of a chromatographic system can minimize the interactions between oligonucleotides and the metallic surfaces of chromatographic flow paths. Consequently, the coated metallic surfaces improve liquid chromatography separations for oligonucleotides. The use of alkylsilyl coatings on metal flow paths allows the use of metal chromatographic flow paths, which are able to withstand high pressures at fast flow rates, while minimizing the secondary chromatographic interactions between oligonucleotides and the metal. These components made of high pressure material and modified with a coating can be tailored so that the internal flow paths reduce secondary chromatographic interactions.

In one aspect, the present technology relates to a method of separating a sample including oligonucleotides. The method includes providing a chromatographic system having a layer of alkylsilyl on at least a portion of a metallic flow path; injecting the sample comprising oligonucleotides into the chromatographic system; flowing the sample through the chromatographic system; and separating the oligonucleotides. The layer of alkylsilyl can include bis(trichlorosilyl)ethane or bis(trimethoxysilyl)ethane.

In one aspect, the present technology relates to a method of separating a sample including a low concentration of analyte. The method includes providing a chromatographic system having a layer of alkylsilyl on at least a portion of a metallic flow path; injecting the sample into the alkylsilyl coated metallic flow path of the chromatographic system; flowing the sample through the alkylsilyl coated metallic flow path of the chromatographic system; separating the sample; and detecting at least an amount of the low concentration of the analyte above a minimum expected value.

The above aspect can include one or more of the following features including comprising recovering greater than 80 percent of the analyte when the low concentration of the analyte extends from about 1 ng/mL to about 5 µg/mL. The layer of alkylsilyl can increase recovery of the analyte with the concentration of analyte extending from about 1 ng/mL to about 5 µg/mL. The layer of alkylsilyl can decrease a minimum concentration of a linear dynamic range of the chromatographic system. The layer of alkylsilyl can also increase the linear dynamic range of the chromatographic system. In some embodiments, the linear dynamic range of the chromatographic system with the layer of alkylsilyl is greater than a chromatographic system without an alkylsilyl coating. The layer of alkylsilyl can include bis(trichlorosilyl)ethane or bis(trimethoxysilyl)ethane.

In a further aspect, the present technology relates to a method of separating a sample. The method includes flowing a first sample comprising oligonucleotides through the system having a fluid-contacting coating on metallic surfaces defining a flow path, wherein the coating comprises an alkylsilyl; separating the first sample; detecting an analyte in the first sample; washing the flow path; flowing a second sample comprising oligonucleotides through the system; separating the second sample; and detecting the second sample, wherein a detected signal from the second sample is within 5% of a detected signal from the first sample and is within 10% of an expected value.

In another aspect, the present technology includes a method of separating a sample. The method includes injecting a first sample comprising oligonucleotides into a system having a fluid-contacting coating on metallic surfaces defining a flow path, wherein the coating comprises an alkylsilyl; flowing the first sample through the system; and detecting oligonucleotides of the first sample at a concentration extending from about 1 ng/mL to about 25 µg/mL (e.g., 1 ng/mL to about 10 µg/mL; 0.1 µg/mL to about 10 µg/mL) when injecting the first sample through the system.

The above aspects and features of the present technology provide numerous advantages over the prior art. For example, in some embodiments, the coated flow path allows for detection of a lower concentration of oligonucleotides, increased accuracy in quantitation of oligonucleotides, the ability to detect oligonucleotides on the first injection, recover an expected amount of oligonucleotides on the first injection, and minimize the amount of injections needed to study a sample.

BRIEF DESCRIPTION OF THE DRAWINGS

The technology will be more fully understood from the following detailed description taken in conjunction with the accompanying drawings, in which:

FIG. 8A is a reversed-phase chromatogram of the first injection of 5 picomoles of deoxythymidine oligomers (15 (SEQ ID NO: 2), 20 (SEQ ID NO: 3), 25 (SEQ ID NO: 4), 30 (SEQ ID NO: 5), and 35-mer (SEQ ID NO: 6)) obtained from a 2.1×50 mm 1.7 µm organosilica 130 Å $C_{18}$ column constructed with an untreated stainless steel (SS) tube and frits, in accordance with an illustrative embodiment of the technology.

FIG. 8B is a reversed-phase chromatogram of the second injection of 5 picomoles of deoxythymidine oligomers (15 (SEQ ID NO: 2), 20 (SEQ ID NO: 3), 25 (SEQ ID NO: 4), 30 (SEQ ID NO: 5), and 35-mer (SEQ ID NO: 6)) obtained from a 2.1×50 mm 1.7 µm organosilica 130 Å $C_{18}$ column constructed with an untreated stainless steel (SS) tube and frits, in accordance with an illustrative embodiment of the technology. FIG. 8B also discloses "dT40" as SEQ ID NO: 7.

FIG. 8C is a reversed-phase chromatogram of the third injection of 5 picomoles of deoxythymidine oligomers (15 (SEQ ID NO: 2), 20 (SEQ ID NO: 3), 25 (SEQ ID NO: 4), 30 (SEQ ID NO: 5), and 35-mer (SEQ ID NO: 6)) obtained from a 2.1×50 mm 1.7 µm organosilica 130 Å $C_{18}$ column constructed with an untreated stainless steel (SS) tube and frits, in accordance with an illustrative embodiment of the technology.

FIG. 8D is a reversed-phase chromatogram of the first injection of 5 picomoles of deoxythymidine oligomers (15 (SEQ ID NO: 2), 20 (SEQ ID NO: 3), 25 (SEQ ID NO: 4), 30 (SEQ ID NO: 5), and 35-mer (SEQ ID NO: 6)) obtained from a column constructed with a $C_2C_{10}$ vapor deposition coated tube and frits, in accordance with an illustrative embodiment of the technology.

FIG. 8E is a reversed-phase chromatogram of the second injection of 5 picomoles of deoxythymidine oligomers (15 (SEQ ID NO: 2), 20 (SEQ ID NO: 3), 25 (SEQ ID NO: 4), 30 (SEQ ID NO: 5), and 35-mer (SEQ ID NO: 6)) obtained from a column constructed with a $C_2C_{10}$ vapor deposition coated tube and frits, in accordance with an illustrative embodiment of the technology.

FIG. 8F is a reversed-phase chromatogram of the third injection of 5 picomoles of deoxythymidine oligomers (15 (SEQ ID NO: 2), 20 (SEQ ID NO: 3), 25 (SEQ ID NO: 4), 30 (SEQ ID NO: 5), and 35-mer (SEQ ID NO: 6)) obtained from a column constructed with a $C_2C_{10}$ vapor deposition coated tube and frits, in accordance with an illustrative embodiment of the technology.

DETAILED DESCRIPTION

In general, the present disclosure solves the problem of not being able to tell when chromatographic systems are fully passivated and ready to operate. By addressing the problematic binding of oligonucleotides on metallic surfaces of chromatographic systems, oligonucleotide bioanalysis can begin within the first or second injection of a sample. In addition, the non-binding of the oligonucleotides improves performance such as limit of detection and linear dynamic range. With decreasing the number of injections to prepare the system by passivation, the time and costs for method development can also be decreased.

In addition, coating the system minimizes uncertainty of the chromatographic system performance. Permanent passivation (or at least semi-permanent passivation, i.e., useable lifetime of a consumable) can be provided by the coating. For example, the system does not need to be passivated after each wash, and passivation does not effectively diminish after each wash or flowing. There is not a question of whether the coating is currently effective and diminishing non-specific binding for oligonucleotides. Consequently, the analyte detected can be depended upon as an accurate assessment of the analyte present.

One method of coating is the use of alkylsilyl coatings. In some aspects, the alkylsilyl coating acts a bioinert, low-bind coating to modify a flow path to address flow path interactions with an analyte, such as oligonucleotides. That is, the bioinert, low-bind coating minimizes surface reactions with the metal interacting oligonucleotides and allows oligonucleotides to pass along a flow path without clogging, attaching to surfaces, or change in analyte properties. The reduction/elimination of these interactions is advantageous because it allows for accurate quantification and analysis of a sample containing oligonucleotides.

Figure 1:
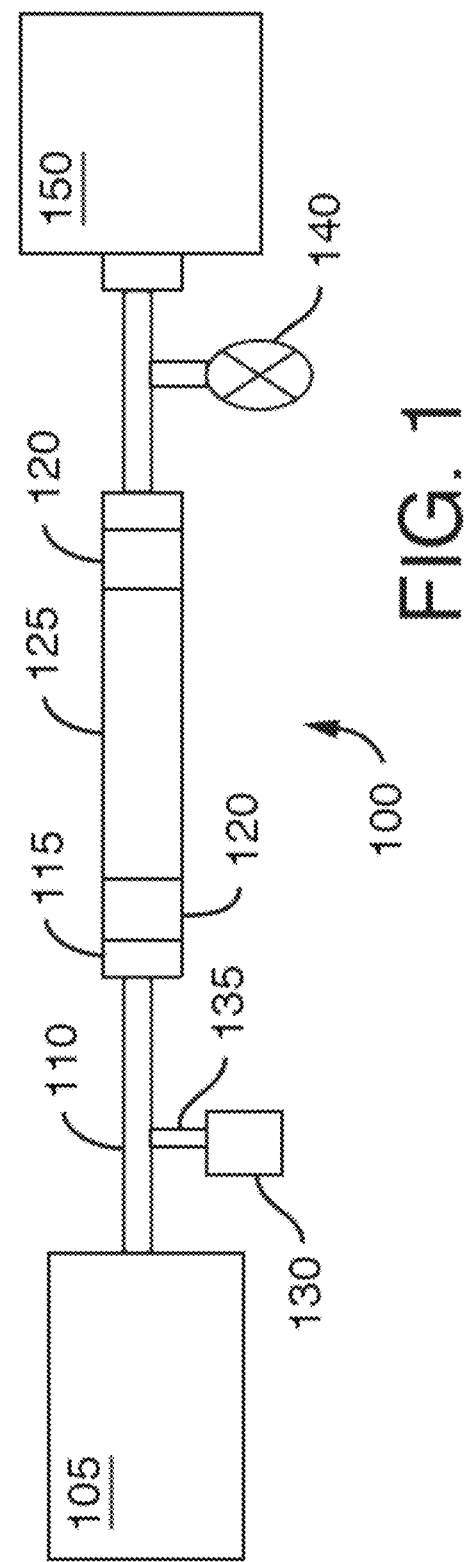
FIG. 1 is a flow chart of a method of separating a sample, according to an illustrative embodiment of the technology.

FIG. 1 is a representative schematic of a chromatographic flow system/device 100 that can be used to separate analytes, such as oligonucleotides, in a sample. Chromatographic flow system 100 includes several components including a fluid manager system 105 (e.g., controls mobile phase flow through the system), tubing 110 (which could also be replaced or used together with micro fabricated fluid conduits), fluid connectors 115 (e.g., fluidic caps), frits 120, a chromatography column 125, a sample injector 135 including a needle (not shown) to insert or inject the sample into the mobile phase, a vial, sinker, or sample reservoir 130 for holding the sample prior to injection, a detector 150, such as a mass spectrometer, and a pressure regulator 140 for controlling pressure of the flow. Interior surfaces of the components of the chromatographic system/device form a fluidic flow path that has wetted surfaces. The fluidic flow path can have a length to diameter ratio of at least 20, at least 25, at least 30, at least 35 or at least 40.

At least a portion of the wetted surfaces can be coated with an alkylsilyl coating to reduce secondary interactions by tailoring hydrophobicity. The coating can be applied by vapor deposition. As such, methods and devices of the present technology provide the advantage of being able to use high pressure resistant materials (e.g., stainless steel) for the creation of the flow system, but also being able to tailor the wetted surfaces of the fluidic flow path to provide the appropriate hydrophobicity so deleterious interactions or undesirable chemical effects on the sample can be minimized. In some examples, the coating of the flow path is non-binding with respect to the analyte, such as oligonucleotides. Consequently, the analyte, such as oligonucleotides, does not bind to the coating of the flow path.

The alkylsilyl coating can be provided throughout the system from the tubing or fluid conduits 110 extending from the fluid manager system 105 all the way through to the detector 150. The coatings can also be applied to portions of the fluidic fluid path. That is, one may choose to coat one or more components or portions of a component and not the entire fluidic path. For example, the internal portions of the column 125 and its frits 120 and end caps 115 can be coated whereas the remainder of the flow path can be left unmodified. Further, removable/replaceable components can be coated. For example, the vial or sinker 130 containing the sample reservoir can be coated as well as frits 120.

In one aspect, the flow path of the fluidic systems described herein is defined at least in part by an interior surface of tubing. In another aspect, the flow path of the fluidic systems described herein is defined at least in part by an interior surface of microfabricated fluid conduits. In another aspect, the flow path of the fluidic systems described herein is defined at least in part by an interior surface of a column. In another aspect, the flow path of the fluidic systems described herein is defined at least in part by passageways through a frit. In another aspect, the flow path of the fluidic systems described herein is defined at least in part by an interior surface of a sample injection needle. In another aspect, the flow path of the fluidic systems described herein extends from the interior surface of a sample injection needle throughout the interior surface of a column. In another aspect, the flow path extends from a sample reservoir container (e.g., sinker) disposed upstream of and in fluidic communication with the interior surface of a sample injection needle throughout the fluidic system to a connector/port to a detector.

In some embodiments, only the wetted surfaces of the chromatographic column and the components located upstream of the chromatographic column are coated with the alkylsilyl coatings described herein while wetted surfaces located downstream of the column are not coated. The coating can be applied to the wetted surfaces via vapor deposition. Similarly, the "wetted surfaces" of labware or other fluid processing devices may benefit from alkylsilyl coatings described herein. The "wetted surfaces" of these devices not only include the fluidic flow path, but also elements that reside within the fluidic flow path. For example, frits and/or membranes within a solid phase extraction device come in contact with fluidic samples. As a result, not only the internal walls within a solid phase extraction device, but also any frits/membranes are included within the scope of "wetted surfaces." All "wetted surfaces" or at least some portion of the "wetted surfaces" can be improved or tailored for a particular analysis or procedure by including one or more of the coatings described herein. The term "wetted surfaces" refers to all surfaces within a separation device (e.g., chromatography column, chromatography injection system, chromatography fluid handling system, frit, etc.). The term can also apply to surfaces within labware or other sample preparation devices (e.g., extraction devices) that come into contact with a fluid, especially a fluid containing an analyte of interest.

At least a portion of the wetted surfaces of the fluidic flow path are coated with an alkylsilyl coating. The alkylsilyl coating is inert to at least oligonucleotides in the sample. The alkylsilyl coating can have the Formula I:

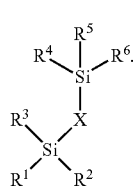

(I)

$R^1$, $R^2$, $R^3$, $R^4$, $R^5$, and $R^6$ are each independently selected from $(C_1-C_6)$alkoxy, —NH$(C_1-C_6)$alkyl, —N$((C_1-C_6)$alkyl$)_2$, OH, OR$^A$, and halo (i.e., a halogen, for example chloro). R$^A$ represents a point of attachment to the interior surfaces of the fluidic system. At least one of $R^1$, $R^2$, $R^3$, $R^4$, $R^5$, and $R^6$ is OR$^A$. X is $(C_1-C_{20})$alkyl, —O[$(CH_2)_2$O]$_{1-20}$—, —$(C_1-C_{10})$[NH(CO)NH$(C_1-C_{10})$]$_{1-20}$—, or —$(C_1-C_{10})$[alkylphenyl$(C_1-C_{10})$alkyl]$_{1-20}$-.

When used in the context of a chemical formula, a hyphen ("-") indicates the point of attachment. For example, when X is —[$(C_1-C_{10})$alkylphenyl$(C_1-C_{10})$alkyl]$_{1-20}$-, that means that X is connected to SiR$^1$R$^2$R$^3$ via the $(C_1-C_{10})$alkyl and connected to SiR$^4$R$^5$R$^6$ via the other $(C_1-C_{10})$alkyl. This applies to the remaining variables.

In one aspect, X in Formula I is $(C_1-C_{15})$alkyl, $(C_1-C_{12})$alkyl, or $(C_1-C_{10})$alkyl. In some aspects, X in Formula I is methyl, ethyl, propyl, isopropyl, butyl, sec-butyl, iso-butyl, t-butyl, pentyl, hexyl, heptyl, nonyl, or decanyl. In other aspect, X in Formula I is ethyl or decanyl.

In one aspect, at least one of $R^1$, $R^2$, $R^3$, $R^4$, $R^5$, and $R^6$ is $(C_1-C_6)$alkoxy, e.g., ethoxy, wherein the values for X are described in Formula I or the preceding paragraph. In another aspect, at least two of $R^1$, $R^2$, $R^3$, $R^4$, $R^5$, and $R^6$ is $(C_1-C_6)$alkoxy, e.g., ethoxy, wherein the values for X are described in Formula I or the preceding paragraph. In another aspect, at least three of $R^1$, $R^2$, $R^3$, $R^4$, $R^5$, and $R^6$ is $(C_1-C_6)$alkoxy, e.g., ethoxy, wherein the values for X are described in Formula I or the preceding paragraph. In another aspect, at least four of $R^1$, $R^2$, $R^3$, $R^4$, $R^5$, and $R^6$ is $(C_1-C_6)$alkoxy, e.g., ethoxy, wherein the values for X are described in Formula I or the preceding paragraph. In another aspect, at least five of $R^1$, $R^2$, $R^3$, $R^4$, $R^5$, and $R^6$ is $(C_1-C_6)$alkoxy, e.g., ethoxy, wherein the values for X are described in Formula I or the preceding paragraph.

In one aspect, at least one of $R^1$, $R^2$, $R^3$, $R^4$, $R^5$, and $R^6$ is halo, e.g., chloro, wherein the values for X are described in Formula I or the preceding paragraphs above. In another aspect, at least two of $R^1$, $R^2$, $R^3$, $R^4$, $R^5$, and $R^6$ is halo, e.g., chloro, wherein the values for X are described in Formula I or the preceding paragraphs above. In another aspect, at least three of $R^1$, $R^2$, $R^3$, $R^4$, $R^5$, and $R^6$ is halo, e.g., chloro, wherein the values for X are described in Formula I or the preceding paragraphs above. In another aspect, at least four of $R^1$, $R^2$, $R^3$, $R^4$, $R^5$, and $R^6$ is halo, e.g., chloro, wherein the values for X are described in Formula I or the preceding paragraphs above. In another aspect, at least five of $R^1$, $R^2$, $R^3$, $R^4$, $R^5$, and $R^6$ is halo, e.g., chloro, wherein the values for X are described in Formula I or the preceding paragraphs above.

In another aspect, $R^1$, $R^2$, $R^3$, $R^4$, $R^5$, and $R^6$ are each methoxy or chloro.

The alkylsilyl coating of Formula I can have a contact angle of at least about 15°. In some embodiments, the alkylsilyl coating of Formula I can have a contact angle of less than or equal to 30°. The contact angle can be less than or equal to about 90°. In some embodiments, the contact angle of the alkylsilyl coating of Formula I is between about 15° to about 105°. For example, the contact angle of the alkylsilyl coating of Formula I can be about 0°, 5°, 10°, 15°, 20°, 25°, 30°, 35°, 40°, 45°, 50°, 55°, 60°, 65°, 70°, 75°, 80°, 85°, 90°, 95°, 100°, or 105°.

The thickness of the alkylsilyl coating can be at least about 100 Å. For example, the thickness can be between about 100 Å to about 1600 Å. Specifically, the alkylsilyl coating on the walls of the flow path can have a thickness of about 100 Å to about 1600 Å. The thickness of the alkylsilyl coating for Formal I can be about 100 Å, 200 Å, 300 Å, 400 Å, 500 Å, 600 Å, 700 Å, 800 Å, 900 Å, 1000 Å, 1100 Å, 1200 Å, 1300 Å, 1400 Å, 1500 Å or 1600 Å. The thickness of the alkylsilyl coating (e.g., a vapor deposited alkylsilyl coating) can be detected optically by the naked eye. For example, more opaqueness and coloration is indicative of a thicker coating. Thus, coatings with pronounced visual distinction are an embodiment of this technology. From thin to thick, the color changes from yellow, to violet, to blue, to slightly greenish and then back to yellow when coated parts are observed under full-spectrum light, such as sunlight. For example, when the alkylsilyl coating is 300 Å thick, the coating can appear yellow and reflect light with a peak wavelength between 560 and 590 nm. When the alkylsilyl coating is 600 Å thick, the coating can appear violet and reflect light with a peak wavelength between 400 and 450 nm. When the alkylsilyl coating is 1000 Å thick, the coating can appear blue and reflect light with a peak wavelength between 450 and 490 nm. See, e.g., Faucheu et al., *Relating Gloss Loss to Topographical Features of a PVDF Coating*, Published Oct. 6, 2004; Bohlin, Erik, *Surface and Porous Structure of Pigment Coatings, Interactions with flexographic ink and effects of print quality*, Dissertation, Karlstad University Studies, 2013:49.

In some examples, coating the flow path includes uniformly distributing the coating about the flow path, such that the walls defining the flow path are entirely coated. Uniformly distributing the coating can provide a uniform thickness of the coating about the flow path. In general, the coating uniformly covers the wetted surfaces such that there are no "bare" or uncoated spots.

In one aspect, the vapor deposited coating of Formula I is the product of vapor deposited bis(trichlorosilyl)ethane, bis(trimethoxysilyl)ethane, bis(trichlorosilyl)octane, bis(trimethoxysilyl)octane, bis(trimethoxysilyl)hexane, and bis(trichlorosilyl)hexane.

In some aspects, at least a portion of the wetted surfaces are coated with multiple layers of the same or different alkysilyls, where the thickness of the alkylsilyl coatings correlate with the number of layering steps performed (e.g., the number of deposited layers of alkylsilyl coating on wetted surfaces (e.g., internal surfaces of the fluidic flow path of the chromatographic system/device or internal surfaces or fluid interfacing/contacting surfaces of labware or other analytical devices, such as frits within a solid phase extraction device together with interior walls of the solid phase extraction device). In this manner, increasingly thick bioinert coatings can be produced and tailored to achieve desirable separations.

The chromatographic device can have a second alkylsilyl coating in direct contact with the alkylsilyl coating of Formula I. The second alkylsilyl coating has the Formula II

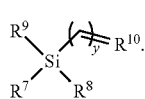

(II)

wherein $R^7$, $R^8$, and $R^9$ are each independently selected from —NH($C_1$-$C_6$)alkyl, —N[($C_1$-$C_6$)alkyl]$_2$, ($C_1$-$C_6$)alkoxy, ($C_1$-$C_6$)alkyl, ($C_1$-$C_6$)alkenyl, OH, and halo; $R^{10}$ is selected from ($C_1$-$C_6$)alkyl, —OR$^B$, —[O($C_1$-$C_3$)alkyl]$_{1-10}$O($C_1$-$C_6$)alkyl, —[O($C_1$-$C_3$)alkyl]$_{1-10}$OH and phenyl. ($C_1$-$C_6$)alkyl is optionally substituted with one or more halo. The phenyl is optionally substituted with one or more groups selected from ($C_1$-$C_3$)alkyl, hydroxyl, fluorine, chlorine, bromine, cyano, —C(O)NH$_2$, and carboxyl. $R^B$ is —($C_1$-$C_3$)alkyloxirane, —($C_1$-$C_3$)alkyl-3,4-epoxycyclohexyl, or —($C_1$-$C_4$)alkylOH. The hashed bond to $R^{10}$ represents an optional additional covalent bond between $R^{10}$ and the carbon bridging the silyl group to form an alkene, provided y is not 0. y is an integer from 0 to 20.

In one aspect, y in Formula II is an integer from 1 to 15. In another aspect, y in Formula II is an integer from 1 to 12. In another aspect, y in Formula II is an integer from 1 to 10. In another aspect, y in Formula II is an integer from 2 to 9.

In one aspect $R^{10}$ in Formula II is methyl and y is as described above for Formula II or the preceding paragraph.

In one aspect, $R^7$, $R^8$, and $R^9$ in Formula II are each the same, wherein $R^{10}$ and y are as described above. In one aspect, $R^7$, $R^8$, and $R^9$ are each halo (e.g., chloro) or ($C_1$-$C_6$)alkoxy such as methoxy, wherein $R^{10}$ and y are as described above.

In one aspect, y in Formula II is 9, $R^{10}$ is methyl, and $R^7$, $R^8$, and $R^9$ are each ethoxy or chloro.

In one aspect, the coating of the formula II is n-decyltrichlorosilane, (3-glycidyloxypropyl)trimethoxysilane (GPTMS), (3-glycidyloxypropyl)trimethoxysilane (GPTMS) followed by hydrolysis, 2-(3,4-epoxycyclohexyl) ethyltrimethoxysilane, trimethylchlorosilane, trimethyldimethyaminosilane, methoxy-polyethyleneoxy(3)silane propyltrichlorosilane, propyltrimethoxysilane, (heptadecafluoro-1,1,2,2-tetrahydrodecyl)tris(dimethylamino)silane, (heptadecafluoro-1,1,2,2-tetrahydrodecyl)trischlorosilane, (heptadecafluoro-1,1,2,2-tetrahydrodecyl)trimethoxysilane vinyltrichlorosilane, vinyltrimethoxysilane, allyltrichlorosilane, 2-[methoxy(polyethyleneoxy)3propyl]trichlorosilane, 2-[methoxy(polyethyleneoxy)3propyl]trimethoxysilane, or 2-[methoxy(polyethyleneoxy)3propyl]tris(dimethylamino) silane.

The alkylsilyl coating of Formula I and II can have a contact angle of at least about 15°. In some embodiments, the alkylsilyl coating of Formula I and II can have a contact angle of less than or equal to 105°. The contact angle can be less than or equal to about 90°. In some embodiments, the contact angle of the alkylsilyl coating of Formula I and II is between about 15° to about 105°. For example, the contact angle of the alkylsilyl coating of Formula I and II can be about 0°, 5°, 10°, 15°, 20°, 25°, 30°, 35°, 40°, 45°, 50°, 55°, 60°, 65°, 70°, 75°, 80°, 85°, 90°, 95°, 100°, or 105°.

The thickness of the multi-layered alkylsilyl coating can be at least about 100 Å. For example, the thickness can be between about 100 Å to about 1600 Å. The thickness of the multi-layered alkylsilyl coating for Formal I can be about 100 Å, 200 Å, 300 Å, 400 Å, 500 Å, 600 Å, 700 Å, 800 Å, 900 Å, 1000 Å, 1100 Å, 1200 Å, 1300 Å, 1400 Å, 1500 Å or 1600 Å.

In one aspect, the alkylsilyl coating of Formula I is bis(trichlorosilyl)ethane or bis(trimethoxysilyl)ethane and the alkylsilyl coating of Formula II is (3-glycidyloxypropyl) trimethoxysilane. In another aspect, the alkylsilyl coating of Formula I is bis(trichlorosilyl)ethane or bis(trimethoxysilyl)ethane and the alkylsilyl coating of Formula II is (3-glycidyloxypropyl)trimethoxysilane followed by hydrolysis. In one aspect, the alkylsilyl coating of Formula I is bis(trichlorosilyl)ethane or bis(trimethoxysilyl)ethane and the alkylsilyl coating of Formula II is n-decyltrichlorosilane. The alkylsilyl coating of Formula I can be bis(trichlorosilyl)ethane or bis(trimethoxysilyl)ethane and the alkylsilyl coating of Formula II can be trimethylchlorosilane or trimethyldimethyaminosilane. In one aspect, the alkylsilyl coating of Formula I is bis(trichlorosilyl)ethane or bis(trimethoxysilyl)ethane and the alkylsilyl coating of Formula II is methoxy-polyethyleneoxy(3) propyl tricholorosilane or methoxy-polyethyleneoxy(3) propyl trimethoxysilane.

The chromatographic device can have an alkylsilyl coating in direct contact with the alkylsilyl coating of Formula III in direct contact with the alkylsilyl coating of Formula I.

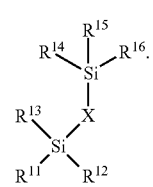

(III)

$R^{11}$, $R^{12}$, $R^{13}$, $R^{14}$, $R^{15}$, and $R^{16}$ are each independently selected from ($C_1$-$C_6$)alkoxy, —NH($C_1$-$C_6$)alkyl, —N(($C_1$-$C_6$)alkyl)$_2$, OH, and halo (i.e., a halogen, for example, chloro). Z is ($C_1$-$C_{20}$)alkyl, —O[($CH_2$)$_2$O]$_{1-20}$—, —($C_1$-$C_{10}$)[NH(CO)NH($C_1$-$C_{10}$)]$_{1-20}$—, or —($C_1$-$C_{10}$)[alkylphenyl($C_1$-$C_{10}$)alkyl]$_{1-20}$-.

In some aspects, Z in Formula III is ($C_1$-$C_{10}$)alkyl; and $R^1$, $R^2$, $R^3$, $R^4$, $R^5$, and $R^6$ are each methoxy or chloro. In other aspects, Z in Formula III is ($C_2$-$C_{10}$)alkyl. In other aspects, Z in Formula III is ethyl.

In the layered alkylsilyl coating of Formula I and Formula III, Formula I and Formula III can be the same (for example, $C_2C_2$) or Formula I and Formula III can be different. Formula III is attached directly to the coating of Formula I, i.e., in Formula III, there is no point of attachment to the interior of the fluidic system; instead Formula III is deposited directly on Formula I.

The alkylsilyl coating of Formula III can be bis(trichlorosilyl)ethane or bis(trimethoxysilyl)ethane. The alkylsilyl coating of Formula I can be bis(trichlorosilyl)ethane or bis(trimethoxysilyl)ethane and the alkylsilyl coating of Formula III can be bis(trichlorosilyl)ethane or bis(trimethoxysilyl)ethane.

The alkylsilyl coating of Formula I and III can have a contact angle of at least about 15°. In some embodiments, the alkylsilyl coating of Formula I and III can have a contact angle of less than or equal to 105°. The contact angle can be less than or equal to about 90°. In some embodiments, the contact angle of the alkylsilyl coating of Formula I and III is between about 15° to about 105°. For example, the contact angle of the alkylsilyl coating of Formula I and III can be about 0°, 5°, 10°, 15°, 20°, 25°, 30°, 35°, 40°, 45°, 50°, 55°, 60°, 65°, 70°, 75°, 80°, 85°, 90°, 95°, 100°, or 105°.

The thickness of the multi-layered alkylsilyl coating can be at least about 100 Å. For example, the thickness can be between about 100 Å to about 1600 Å. The thickness of the multi-layered alkylsilyl coating for Formal I can be about 100 Å, 200 Å, 300 Å, 400 Å, 500 Å, 600 Å, 700 Å, 800 Å, 900 Å, 1000 Å, 1100 Å, 1200 Å, 1300 Å, 1400 Å, 1500 Å or 1600 Å.

In one aspect, the alkylsilyl coating of Formula II is applied directly to wetted surfaces of the fluidic flow path. Therefore, in some embodiments, one of $R^7$, $R^8$, and $R^9$ of Formula II can also include $OR^A$, where $R^A$ represents a point of attachment to the interior surfaces (e.g., wetted surfaces) of the fluidic system. In other embodiments, $R^7$, $R^8$, and $R^9$ of the alkylsilyl coating of Formula II does not include $OR^A$, by the alkylsilyl coating of Formula II is deposited directly onto wetted surfaces of the fluidic flow path that have been pre-treated with, for example, a plasma.

In one aspect, stainless steel flow path components, including but not limited to tubing, microfabricated fluid conduits, column fits, column inlet tubing, and sample injection needles, are coated via vapor deposition with one or more of the disclosed alkylsilyls. In one aspect, these coated components are annealed to alter their chemical or physical properties.

Exemplary coatings with their respective approximate thickness and contact angle are provided in Table 1.

TABLE 1

| VPD # | Vapor Deposited Material | Alternative Coating Abbreviation | Approximate Thickness of Product | Approximate Contact Angle |
| --- | --- | --- | --- | --- |
| 1 | bis(trichlorosilyl)ethane or bis(trismethoxysilyl)ethane as a first layer followed by GPTMS followed by hydrolysis to form GPTMS-OH | $C_2$-GPTMS-OH | 500 Å | 15° |
| 2 | bis(trichlorosilyl)ethane or bis(trimethoxysilyl)ethane | $C_2$ | 500 Å | 35° |
| 3 | bis(trichlorosilyl)ethane or bis(trimethoxysilyl)ethane as a first layer followed by bis(trichlorosilyl)ethane or bis(trimethoxysilyl)ethane as a second layer. | $C_2$-$C_2$ | 1600 Å | 35° |
| 4 | bis(trichlorosilyl)ethane or bis(trimethoxysilyl)ethane as a first layer followed by GPTMS as a second layer | $C_2$-GPTMS | 500 Å | 50° |
| 5 | Annealed bis(trichlorosilyl)ethane or bis(trimethoxysilyl)ethane | Annealed $C_2$ | 500 Å | 95° |
| 6 | Annealed bis(trichlorosilyl)ethane or bis(trimethoxysilyl)ethane as a first layer followed by annealed bis(trichlorosilyl)ethane or bis(trimethoxysilyl)ethane as a second layer | Annealed $C_2$-$C_2$ | 1600 Å | 95° |
| 7 | bis(trichlorosilyl)ethane or bis(trimethoxysilyl)ethane as a first layer followed by n-decyltrichlorosilane as a second layer | $C_2C_{10}$ | 500 Å | 105° |
| 8 | Annealed bis(trichlorosilyl)ethane or bis(trimethoxysilyl)ethane as a first layer followed by annealed n-decyltrichlorosilane as a second layer | Annealed $C_2C_{10}$ | 500 Å | 105° |
| 9 | GPTMS | GPTMS | 100 to 200 Å | ~50° |
| 10 | GPTMS followed by hydrolysis to form GPTMS-OH | GPTMS-OH | 100 to 200 Å | ~20° |
| 11 | bis(trichlorosilyl)ethane or bis(trimethoxysilyl)ethane as a first layer followed by trimethylchlorosilane or trimethyldimethylaminosilane | $C_2C_3$ | 500 Å | 40-90° |
| 12 | annealed | Annealed | 500 Å | 95° |

TABLE 1-continued

| VPD # | Vapor Deposited Material | Alternative Coating Abbreviation | Approximate Thickness of Product | Approximate Contact Angle |
|---|---|---|---|---|
|  | bis(trichlorosilyl)ethane or bis(trimethoxysilyl)ethane as a first layer followed by trimethylchlorosilane or trimethyldimethylaminosilane | C₂C₃ |  |  |
| 13 | bis(trichlorosilyl)ethane or bis(trimethoxysilyl)ethane as a first layer followed by a methoxy-polyethyleneoxy(3) propyl trichlorosilane or methoxy-polyethyleneoxy(3) propyl trimethoxysilane | C₂PEO | 500 Å | 15° |

Referring to VPD #1 (C₂-GPTMS-OH), the first coating layer, C₂ shown below, is a layer according to Formula I, described above.

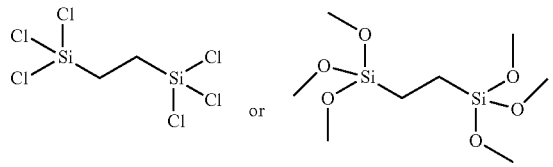

structure of bis(trichlorosilyl)ethane or bis(trimethoxysilyl)ethane (C₂)

The second layer of VPD #1, GPTMS-OH, shown below, is a layer according to Formula II.

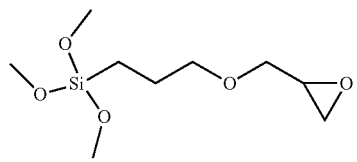

Structure of GPTMS-OH

VPD #3 (C₂-C₂) is an example of a coating of Formula I and then a coating for Formula III.

VPD #7 (C₂C₁₀) is another example of a coating of Formula I and a second layer of Formula II. The structure of bis(trichlorosilyl)ethane or bis(trimethoxysilyl)ethane (C₂) is shown above. The structure of C₁₀ is shown below.

Structure of n-decyltrichlorosilane (C₁₀)

VPD #11 (C₂C₃) is another example of a coating of Formula I and a second layer of Formula II. The structure of bis(trichlorosilyl)ethane or bis(trimethoxysilyl)ethane (C₂) is shown above. The structure of C₃ is shown below.

Structure of trimethylchlorosilane or trimethyldimethylaminosilane (C₃)

VPD #13 is another example of a coating of Formula I and a second layer of Formula II. The structure of bis(trichlorosilyl)ethane or bis(trimethoxysilyl)ethane (C₂) is shown above. The structure of methoxy-polyethyleneoxy(3)propyl trichlorosilane (PEO) is shown below.

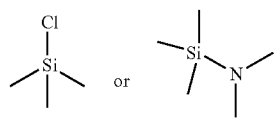

Structure of methoxy-polyethyleneoxy(3)propyl trichlorosilane (PEO)

Alternatively, commercially available vapor deposition coatings can be used in the disclosed systems, devices, and methods, including but not limited to Dursan® and Dursox® (commercially available from SilcoTek Corporation, Bellefonte, PA).

In one aspect, the alkylsilyl coatings described herein enhance the corrosion performance of metals, e.g., as in metallic chromatography columns. Depending on the denseness and thickness, the coatings act as a barrier, thereby preventing water and corrosive molecules from reacting with the base metal. The alkylsilyl coatings can be hydrophobic. While increasing the hydrophobicity and density improves the corrosion performance, even coatings derived from $C_2$ and GPTMS ($C_2$-GPTMS) followed by hydrolysis to form $C_2$-GPTMS-OH shows a 10× improvement in the ASTM G48 Method A pitting corrosion. In terms of most corrosion resistant to least, the ranking is the material formed from VPD #7>2>1 (bis(trichlorosilyl)ethane or bis(trimethoxysilyl)ethane as a first layer followed by GPTMS then hydrolysis to form GPTMS-OH as a second layer). This also correlates to hydrophobicity rankings.

The coatings described above can be used to tailor a fluidic flow path of a chromatography system for the separation of a sample. The coatings can be vapor deposited. In general, the deposited coatings can be used to adjust the hydrophobicity of internal surfaces of the fluidic flow path that come into contact with a fluid (i.e. wetted surfaces or surfaces coming into contact with the mobile phase and/or sample/analyte). By coating wetted surfaces of one or more components of a flow path within a chromatography system, a user can tailor the wetted surfaces to provide a desired interaction (i.e., a lack of interaction) between the flow path and fluids therein (including any sample, such as a sample containing oligonucleotides, within the fluid).

Non-specific binding of oligonucleotides within chromatographic systems negatively impacts the ability to detect and accurately quantify these molecules. The mechanism of non-specific binding is due to the interaction of the analyte with metallic surfaces in the flow path. The present disclosure relates to the use of a coating to reduce non-specific binding in chromatographic systems to improve performance, e.g., limit of detection, initial performance, peak shape, retention times, accurate quantitation, repeatability of analysis, speed to result, and linear dynamic range, for oligonucleotide bioanalysis.

In one aspect, an effective coating is produced from a low temperature, vacuum-assisted vapor deposition process. In one aspect, an oxygen plasma pretreatment step precedes the coating deposition. The oxygen plasma removes organic compounds and improves surface wettability for the coatings. Time, temperature, and pressure are controlled for each processing step. Each coating run can use a silicon wafer to monitor the thickness and contact angle of the resultant coating. Ellipsometry can be used to measure the coating thickness, and an optical goniometer can be used to measure the contact angle of the coating. A post coating annealing step can be utilized to increase coating cross-linking and increase coating hydrophobicity.

Further information regarding deposition of coatings in accordance with the present technology is available in US 2019/0086371, which is hereby incorporated by reference.

Figures 2, 3:
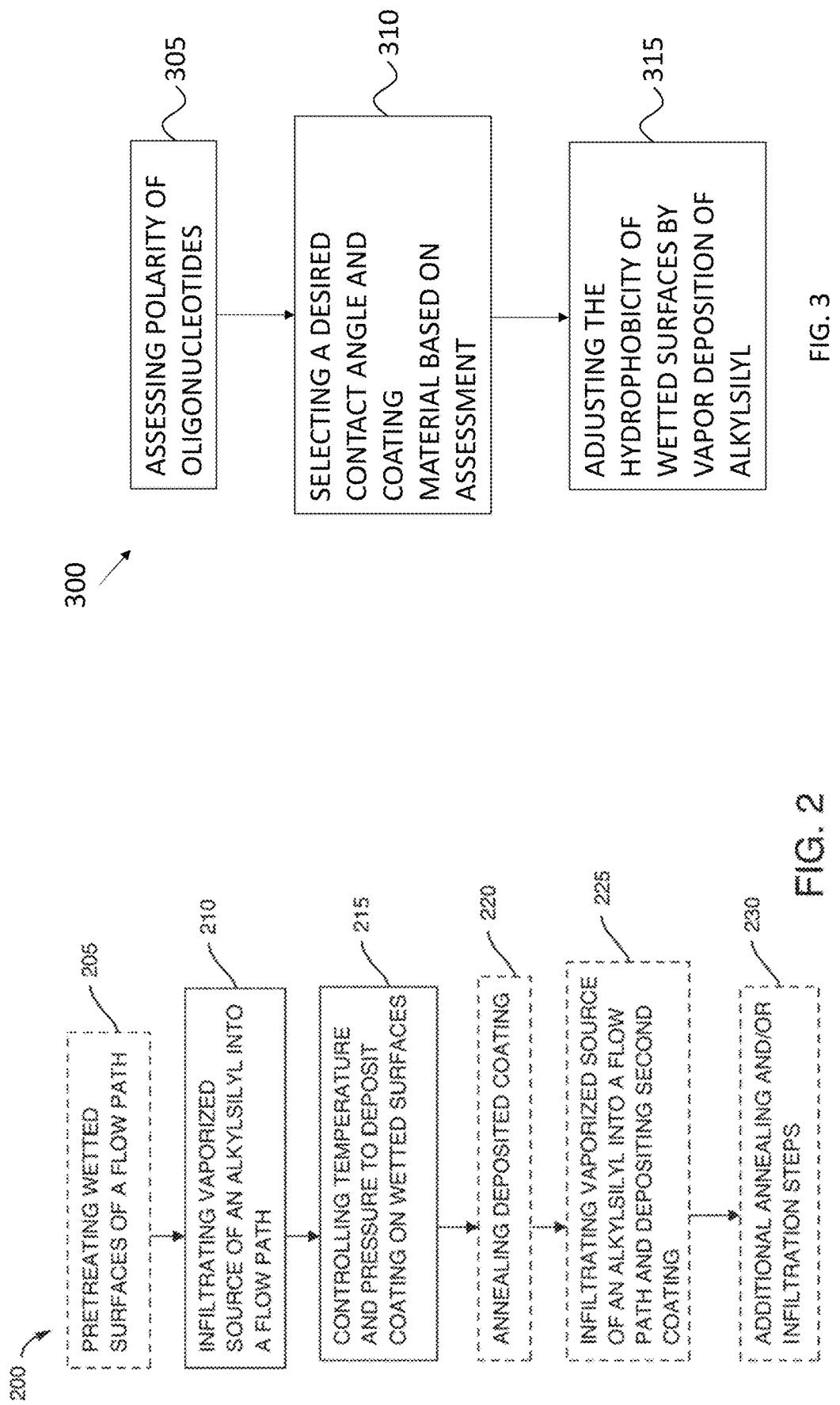
FIG. 2 is a flow chart of a method of performing solid phase extraction, according to an illustrative embodiment of the technology.
FIG. 3 is a flow chart showing a method of tailoring a fluidic flow path for separation of a sample including a biomolecule, in accordance with an illustrative embodiment of the technology.

FIG. 2 is a flow chart illustrating method 200 for tailoring a fluidic flow path for separation of a sample including oligonucleotides. The method has certain steps which are optional as indicated by the dashed outline surrounding a particular step. Method 200 can start with a pretreatment step (205) for cleaning and/or preparing a flow path within a component for tailoring. Pretreatment step 205 can include cleaning the flow path with plasma, such as oxygen plasma. This pretreatment step is optional.

Next, an infiltration step (210) is initiated. A vaporized source of an alkylsilyl compound (e.g., the alkylsilyl compounds of Formulas I, II and/or III) is infiltrated into the flow path. The vaporized source is free to travel throughout and along the internal surfaces of the flow path. Temperature and/or pressure is controlled during infiltration such that the vaporized source is allowed to permeate throughout the internal flow path and to deposit a coating from the vaporized source on the exposed surface (e.g., wetted surfaces) of the flow path as shown in step 215. Additional steps can be taken to further tailor the flow path. For example, after the coating is deposited, it can be heat treated or annealed (step 220) to create cross linking within the deposited coating and/or to adjust the contact angle or hydrophobicity of the coating. Additionally or alternatively, a second coating of alkylsilyl compound (having the same or different form) can be deposited by infiltrating a vaporized source into the flow path and depositing a second or additional layers in contact with the first deposited layer as shown in step 225. After the deposition of each coating layer, an annealing step can occur. Numerous infiltration and annealing steps can be provided to tailor the flow path accordingly (step 230).

FIG. 3 provides a flow chart illustrating a method (300) of tailoring a fluidic flow path for separation of a sample including a analyte, such as oligonucleotides. The method can be used to tailor a flow system for use in isolating, separating, and/or analyzing oligonucleotides. In step 305, oligonucleotides are assessed to determine polarity. Understanding the polarity will allow an operator to select (by either look up table or make a determination) a desired coating chemistry and, optionally, contact angle as shown in step 310.

In some embodiments, in addition to assessing the polarity of oligonucleotides, the polarity of a stationary phase to be used to separate the oligonucleotides (e.g., stationary phase to be included in at least a portion of the fluidic flow path) is also assessed. A chromatographic media can be selected based on oligonucleotides in the sample. Understanding the polarity of both the oligonucleotides and the stationary phase is used in certain embodiments by the operator to select the desired coating chemistry and contact angle in step 310. The components to be tailored can then be positioned within a chemical infiltration system with environmental control (e.g., pressure, atmosphere, temperature, etc.) and precursor materials are infiltrated into the flow path of the component to deposit one or more coatings along the wetted surfaces to adjust the hydrophobicity as shown in step 315. During any one of infiltration, deposition, and condition steps (e.g. annealing), coatings deposited from the infiltration system can be monitored and if necessary precursors and or depositing conditions can be adjusted if required allowing for fine tuning of coating properties. The alkylsilyl coating material selected in step 310 can be the alkylsilyl compounds of Formulas I, II and/or III. For example, the alkylsilyl coating could be an organosilica coating with Formula I ($C_2$ coating described above). The alkylsilyl coating need not be selected from these formulas. That is, other materials are available for use as the coating material. A possible coating material includes any deposited coating that is hydrophobic.

The method also includes adjusting a hydrophobicity of the wetted surfaces of the fluidic flow path by vapor depositing the alkylsilyl coating onto the wetted surfaces of the fluidic flow path. In some embodiments, the hydrophobicity of the wetted surfaces is adjusted by adjusting the contact angle of the alkylsilyl coating. For example, the contact angle of the alkylsilyl coating can be between about 0° to about 105°.

The analyte in the sample can be retained with a retentivity within 10% of the retentivity attributable to the chromatography media. In some embodiments, the sample can be retained with a retentivity within 5% or within 1% of the retentivity attributable to the chromatography media. Therefore, the alkylsilyl coating solves the problem of metal interaction between the analyte and the metal chromatographic materials without introducing any secondary reactions that would have a negative effect on the quality of the separation. The alkylsilyl coating does not impart any retention mechanism on the analyte of interest, making the coating inert to the analyte of interest and low-binding.

In some embodiments, the alkylsilyl coating is modified with a silanizing reagent to obtain a desired thickness of the alkylsilyl coating. The silanizing reagent can be a non-volatile zwitterion. The non-volatile zwitterion can be sulfobetaine or carboxybetaine. In some embodiments, the silanizing reagent is an acidic or basic silane. The silanizing reagent can introduce polyethylene oxide moieties, such as methoxy-polyethyleneoxy(6-9)silane, the structure of which is shown below.

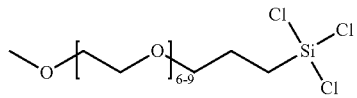

Structure of methoxy-polyethyleneoxy(6-9)silane

In some aspects, the method of tailoring a fluidic flow path for separation of a sample includes pretreating the wetted surfaces of the flow path with a plasma prior to depositing the first coating, annealing the first coating at a temperature to increase cross-linking in the first coating, and/or annealing the first coating at a temperature to alter hydrophobicity.

Non-Specific Binding

Due to prevention of non-specific binding of oligonucleotides in the flow path, a sample with a low concentration of oligonucleotides can still recover oligonucleotides. This is especially pronounced at lower concentrations because the percentage of analyte that is bound to the surface is high relative to the total concentration. In some examples, chromatographic systems can recover greater than 80 percent of the analyte when the low concentration of the analyte extends from about 1 ng/mL to about 25 μg/mL.

In some examples, chromatographic systems can recover greater than 80, 85, 90, or percent of the analyte in a first injection. FIG. 8A shows a first injection of dT15 (SEQ ID NO: 2) on an uncoated stainless steel tube and frit. The area recovered is only 67% of the area observed from the third injection (FIG. 8C). In contrast, FIG. 8D illustrates the same sample injected onto a coated flow path (i.e., a coated flow path in accordance with the present technology). In this example, the first injection on the system is 98% of the area observed when compared to the third injection (FIG. 8F). In some examples, the first injection of chromatographic system can recover an analyte with a low concentration of about 1 ng/mL to about 25 μg/mL; 1 ng/mL to about 10 μg/mL; 0.1 μg/mL to about 5 μg/mL; 0.1 μg/mL to about 1 μg/mL; less than 10 μg/mL; or less than 5 μg/mL.

The present technology provides an advantage over the non-coated flow paths in that such low concentrations are usually not detectable. That is, the low concentration samples easily bind to the metallic surfaces—and passivation would take too long or require too much sample.

injecting the sample is a first injection, and detecting includes detecting the analyte after the first injection when the low concentration of the analyte extends from about 1 ng/mL to about 5 μg/mL or from 1 ng/mL to about 25 μg/mL.

The present technology provides an advantage over the non-coated flow paths in that on the first injection an analyte can be recovered. In addition, not only can an analyte be recovered but the amount of analyte recovered is an accurate representation of the amount of analyte in the sample. For example, coating the flow path of the chromatographic system increases recovery of the analyte with the concentration of the analyte extending from about 1 ng/mL to about 5 μg/mL. As a comparison, recovery of oligonucleotides on a first injection can increase by 20 percent (or more, e.g., 25%, 30%, 40%, 50%, 60%, 70%, 80, 85%, 90%, 100%) by coating the flow path of the chromatographic system.

Without wishing to being bound by theory, the mechanism of non-specific binding is due to the interaction of the analyte with metallic surfaces in the flow path. Due to the presence of multiple phosphate groups, oligonucleotides are excellent polydentate ligands capable of high affinity metal chelation. This interaction leads to a reduced amount of analyte detected and inaccurate quantitation. This becomes especially pronounced at lower concentrations where the percentage of analyte that is bound to the surface is very high relative to the total concentration. The impact of performance claims from the analytical methods, such as limit of detection and linear dynamic range, are compromised due to this unwanted interaction.

The present technology provides an advantage over the non-coated flow paths in that coating the flow path of the chromatographic system increases a linear dynamic range of the chromatographic system. A linear dynamic range of the chromatographic system with the coating is greater than a chromatographic system without the coating. For example, coating the chromatographic system can decrease a minimum concentration of a linear dynamic range of the chromatographic system. With a constant maximum concentration of the linear dynamic range of the chromatographic system, the linear dynamic range will be increased because the minimum concentration of the linear dynamic range has decreased. Stated another way, the linear dynamic range increases because the maximum concentration stays constant while the minimum increases.

As stated herein, a first injection can have a high percentage of analyte recovered. In some examples, the amount of analyte recovered will remain substantially constant over the first injections. Consequently, a minimum of a linear dynamic range of the chromatographic system can remains substantially similar over the first 50 injections.

Non-specific binding (e.g., mostly on metallic frits, partially on column hardware and tubing) often alters the chromatographic peak shape. Peaks can tail to the extent it is difficult to integrate them. By coating the fluid flow path to prevent non-specific binding, chromatographic peak shape will be more accurate on the first injection. Consequently, chromatographic peak shape can be predicted for samples with known oligonucleotides. The actual versus expected chromatographic peak shape can be compared. In some examples, a chromatographic peak shape of the analyte of the separated sample can be substantially similar to a reference chromatographic peak shape. Also, coating the flow path of the liquid chromatography column increases the similarity between a chromatographic peak shape of the analyte of the separated sample and a reference chromatographic peak shape.

In addition, the coating (e.g., an alkylsilyl coating) in some embodiments does not produce any changes to peak width. The analyte in the sample has a peak width that is within 10%, 5%, or 1% of the peak width attributable to the chromatographic media.

Also, non-specific binding will shift retention times (non-specific binding contributes to retention), so the retention time can be hard to control as the column is being passivated by injections of sample. Thus, by coating the flow paths (e.g., entire wetted flow path including injection mechanisms, frits, connectors, etc.), a permanent (or semi-permanent) passivation is created—that does not wash away or dissipate during wash cycles or after stopping flow of a sample.

Examples

Example 1: Improved Limit of Detection

Figure 4:
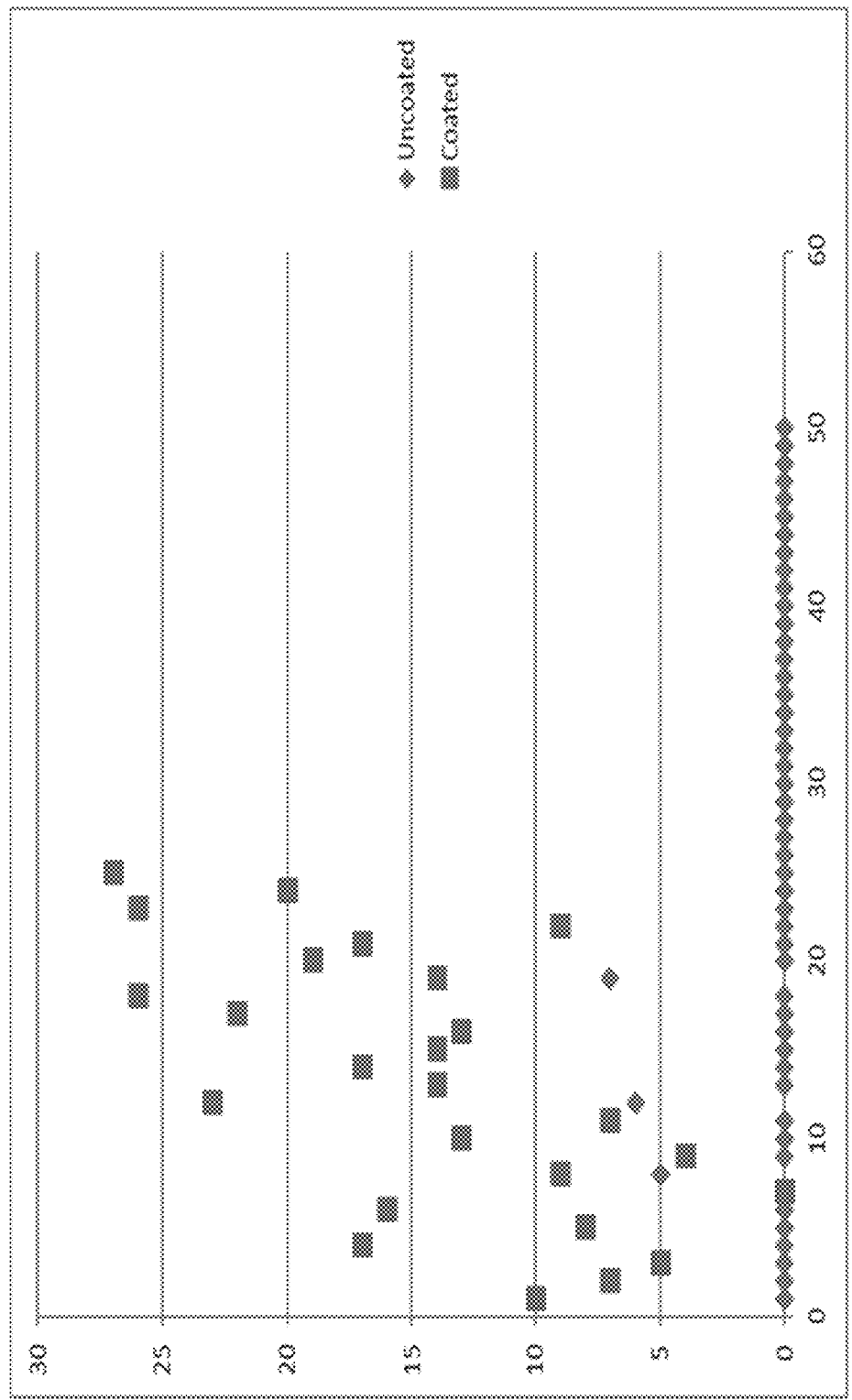
FIG. 4 is a graph showing the injection of 0.6 µg/mL of GEM 91 oligonucleotides on an uncoated (diamond) and coated (square) system.

LC/MS data for a fully thiolated 25-mer (GEM 91 oligonucleotides) was acquired using both coated and uncoated systems and the results were compared (FIG. 4). Injection of 0.6 µg/mL of GEM 91 oligonucleotides on an uncoated (diamond plot points) and coated (square plot points) system. Initial performance observations of the uncoated system showed that no analyte signal was detected after multiple injections of GEM 91 oligonucleotides (diamond). Overlaid with this the data from the coated system (squares). This result demonstrates that even from the very first injection, the coated system has better initial performance that the uncoated system for oligonucleotide analysis. Improved limit of detection can be seen as in the coated system of the present technology is instantaneous whereas, for the uncoated system, there is still no observed signal for the analyte after 50 injections.

Additional improvements over the uncoated technology are also achieved by the present disclosure. For example, significant gains are achieved with respect to the limit of quantitation (LOQ). Specifically, a calibration curve for an uncoated flow path is known to start out at a very low concentration and increase. The data of FIG. 4 shows that for the coated column of the present technology is substantially constant and above the LOQ. Further, the same data demonstrates improved limit of detection (LOD) with a coated column. That is, the analyte signal with an uncoated column is still below limit of quantitation (BLOQ) after 50 injections, whereas the coated column is above the LOQ on the first injection (See FIG. 5).

Example 2: Improved Initial Performance

Figure 5:
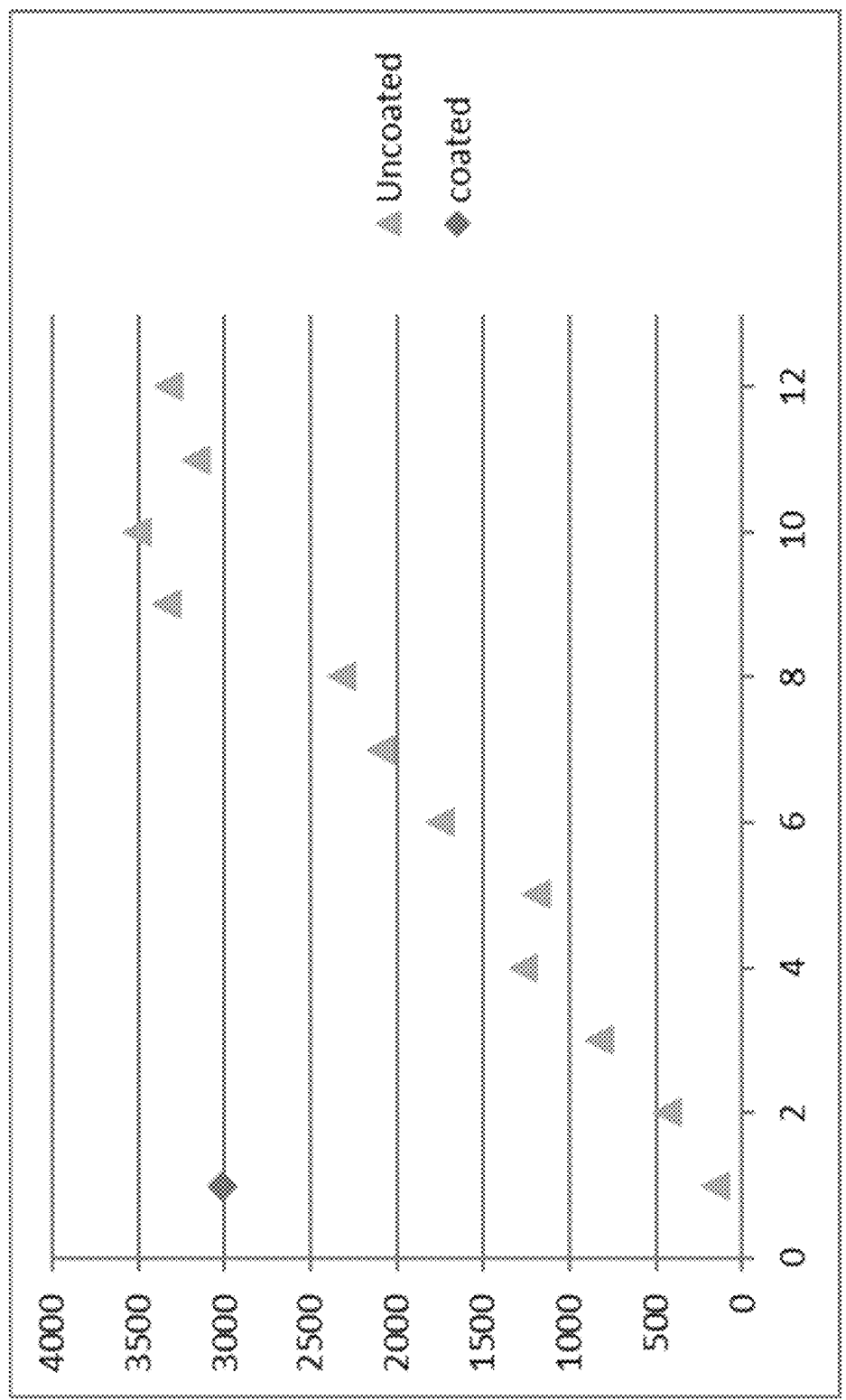
FIG. 5 is a graph showing the injection of 6 µg/mL of GEM 91 oligonucleotides on an uncoated (triangle) and coated (diamond) system.

The performance gains as shown in Example 1 are further demonstrated when injecting a higher concentration sample. FIG. 5 shows an injection of 6 µg/mL of GEM 91 oligonucleotides on an uncoated (triangle) and coated (diamond) system. That is a ten times (10×) greater concentration of the same analyte as Example 1. The uncoated system doesn't reach the expected signal of 300 area counts until the 9$^{th}$ injection. The coated system was able to obtain the expected result on the first injection. This data was acquired after the previous 50 injections so the uncoated column performance was probably almost passivated.

These samples, injected immediately after the lower concentration samples from Example 1, show that the uncoated system (triangle) required nine injections to equilibrate and reach the performance of a fully passivated system (triangle). As indicated previously, the coated system (diamond) was able to reach the performance specification on its first injection.

Examples 3 and 4: Multiple Injections in Single Experimental Run (MISER)

MISER enables fast analyses and visualization of series of injections.

Experimental set-up including bio-inert hardware: H-Class Bio modified with a coating to create a low bind surfaces (LBS). LBS are based on chemical coating on metallic surfaces. Stainless steel or titanium frits were coated by $C_2$ or $C_2C_{10}$ coatings and then investigated. The coated and uncoated frits housed in the holder were placed in the mobile phase flow path in place of the column.

LBS can improve analyte recovery and peak shape. Bio-inert LC systems can include LBS as the wetted surfaces. LBS is applicable to column hardware.

Figure 6:
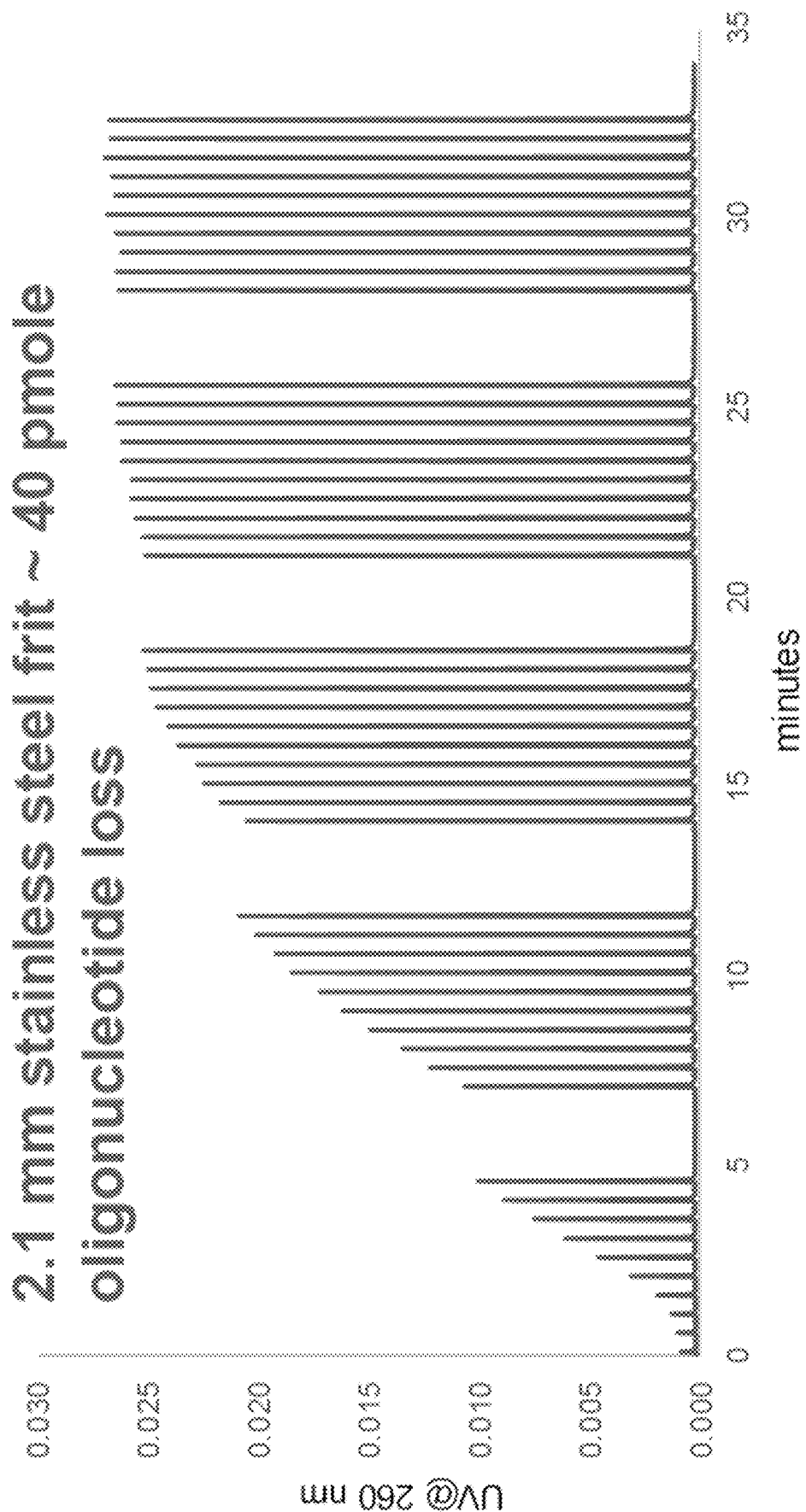
FIG. 6 is a graph of 50 injections of 25mer oligonucleotide (2.6 pmole per injection) on H-Class Bio with stainless steel frit in flow path.

For Example 3, no column was used. All the observed sample loss is due to single frit. The frit was chosen because it has the most significant surface area—the most obvious impact on sample recovery. The mobile phase was 10 mM ammonium acetate, pH ~7 in 50% ACN. FIG. 6 shows 50 injections of 25mer oligonucleotide (2.6 pmole per injection) on H-Class Bio with stainless steel frit in flow path. Non-specific frit adsorption is saturated after ~40 injections. Cumulative estimated loss is ~40 pmoles of oligonucleotide.

Figure 7:
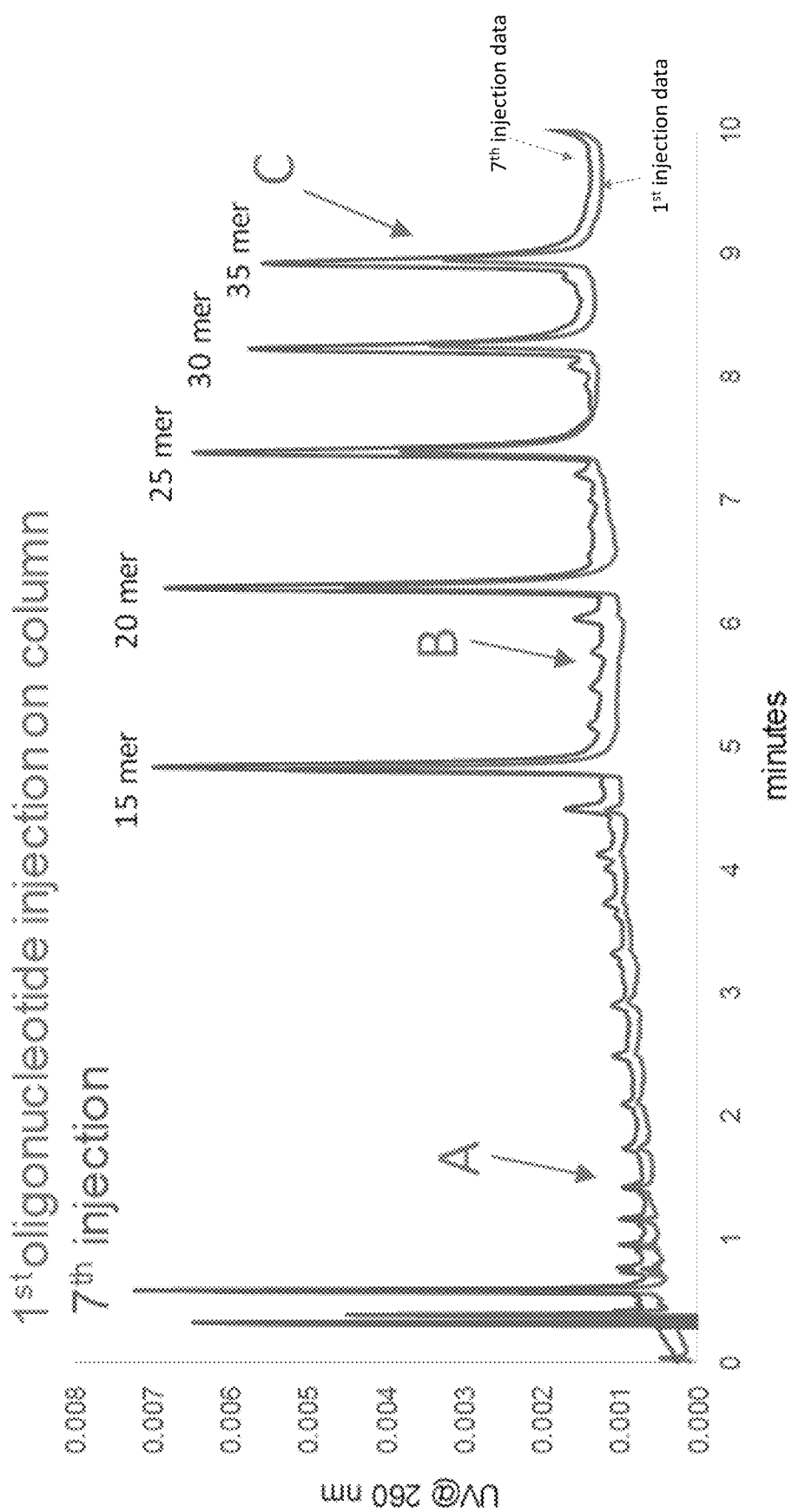
FIG. 7 is a graph of oligonucleotide standard, 15-35 mer, injection of 10 pmol on BEH C18 50×2.1, 1.7 µm column.
Figure 9:
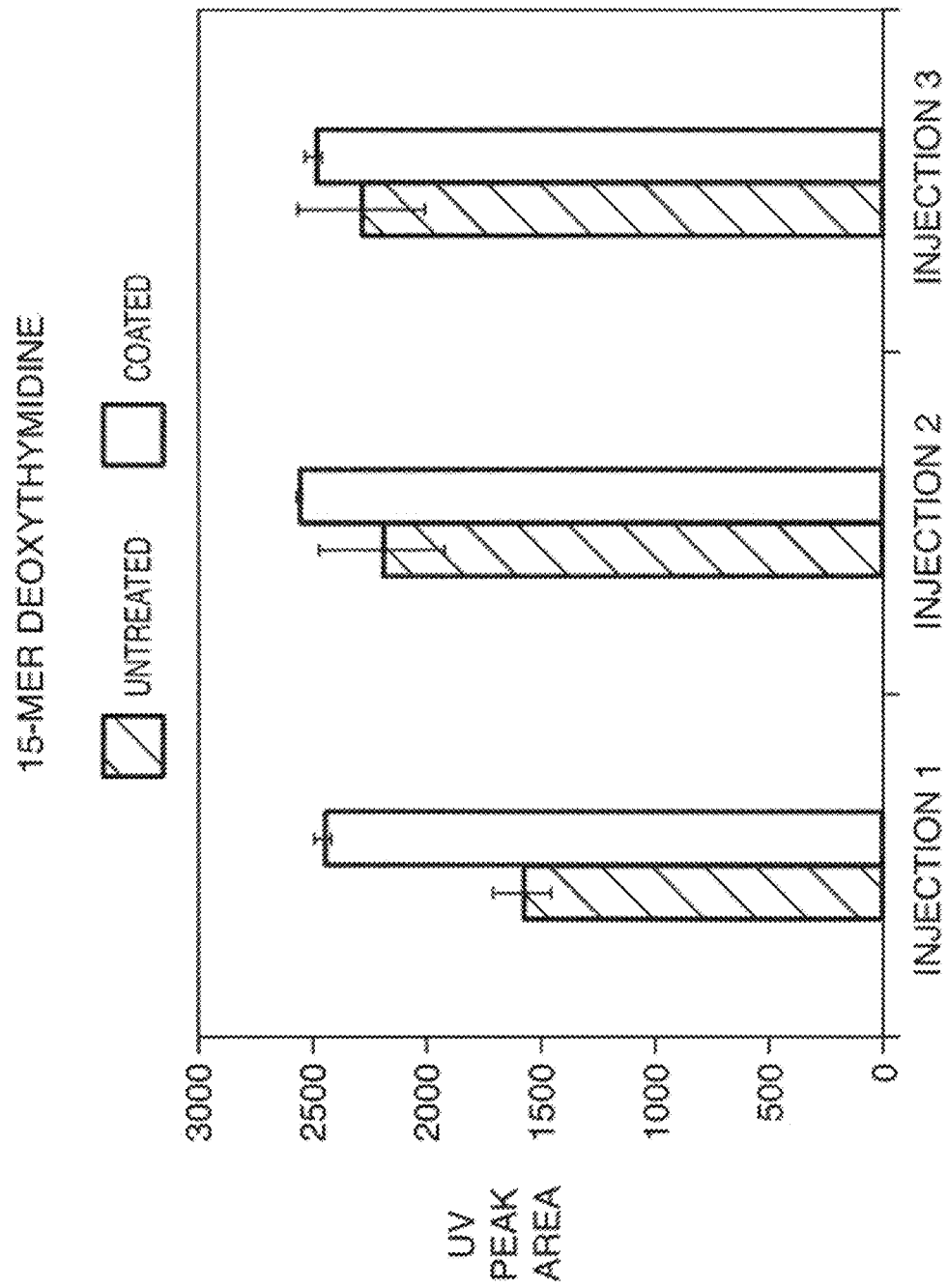
FIG. 9 is a graph showing the average UV peak areas of a 15-mer deoxythymidine analyte (SEQ ID NO: 2) as observed during reversed phase chromatography and initial injections onto either a 2.1×50 mm 1.7 µm organosilica 130 Å $C_{18}$ column constructed with untreated stainless steel (SS) or $C_2C_{10}$ vapor deposition coated components, in accordance with an illustrative embodiment of the technology. Analyses were performed in duplicate using two untreated columns and two $C_2C_{10}$ vapor deposition coated columns.

For Example 4, conventional column (two stainless steel frits) was used for separation of oligonucleotides. FIG. 7 shows oligonucleotide standard, 15-35 mer, injection of 10 pmol on BEH C18 50×2.1, 1.7 µm column. See the portion indicated by the "A" arrow for acceptable recovery of short oligonucleotides; "B" arrow for loss of minor oligonucleotide peaks in first injection; and "C" arrow for loss of recovery for long oligonucleotides. The first oligonucleotide injection on the column is the lower line, and the seventh oligonucleotide injection on the column is the top line. The mobile phase was 0.1M TEAA, pH 7, 8 to 12% ACN in 10 minutes.

Example 5: $C_2$ and $C_2C_{10}$ Vapor Deposition Coatings

Prior to coating, all metal components are passivated according to a nitric acid passivation. Passivated parts and a silicon wafer are then introduced to the vapor deposition chamber and vacuum is established. The first step is a 15 minute, 200 Watt, 200 cc/min oxygen plasma cleaning step. Next is the first vapor deposition cycle. Each vapor deposition cycle contains a silane vapor deposition, followed by the introduction of water vapor for silane hydrolysis. The silane vapor is delivered at a pressure of 2.0 Torr for 5 seconds, and then the water vapor is delivered at a pressure of 50 Torr for 5 seconds. Following delivery, the silane and water is left to react with the substrate for 15 minutes. This cycle is repeated to produce the desired number of layers and coating thickness. An additional processing cycle can be implemented to functionalize the coating with yet another silane. Moreover, a post coating annealing step can be used to further cross-link and increase the hydrophobicity of the coating. Typically, the annealing cycle involves subjecting the coating to 200° C. for 3 hours under vacuum.

A silicon wafer is used as a coupon to measure the thickness and contact angle of the coating. To measure the thickness, a Gaertner Scientific Corporation stokes ellipsometer model LSE is used. By analyzing the change in polarization of light, and comparing to a model, the film thickness can be established. To measure the contact angle, a Ramé-Hart goniometer model 190 is used. After dropping a controlled amount of water onto a perfectly level silicon wafer, optical techniques are used to measure the contact angle.

Example 6: $C_2$-GPTMS-OH Vapor Deposition Coatings

Prior to coating, all metal components are passivated according to a nitric acid passivation. Passivated parts and a silicon wafer are then introduced to the vapor deposition chamber and vacuum is established. The first step is a 15 minute, 200 Watt, 200 cc/min oxygen plasma cleaning step. Next is the first vapor deposition cycle. Each vapor deposition cycle contains a silane vapor deposition, followed by the introduction of water vapor for silane hydrolysis. The silane vapor is delivered at a pressure of 2.0 Torr for 5 seconds, and then the water vapor is delivered at a pressure of 50 Torr for 5 seconds. Following delivery, the silane and water is left to react with the substrate for 15 minutes. This cycle is repeated to produce the desired number of layers and coating thickness. In this example, the bis(trichlorosilyl) ethane silane is used to build up an adhesion or primer layer of approximately 800 Å. After $C_2$ deposition, the 3-(glycidoxypropyl)trimethoxysilane is delivered anhydrously to a pressure of 0.4 Torr in the vapor deposition chamber. This silane vapor is left to react with the $C_2$ coated substrate for one hour. This process results in an epoxide terminated coating, with a contact angle of 50°. After deposition, the next step is to hydrolyze the epoxide groups. This is performed either in the liquid phase or the vapor phase, with 0.1M acetic acid. After epoxide hydrolysis, the contact angle is <20°. Contact angle measurements are taken on a silicon wafer using a Ramé-Hart goniometer model 190.

Example 7: Oligonucleotide Ion Pair RPLC

Testing has shown that flow paths modified with the vapor deposition coatings of the present disclosure are also helpful in improving oligonucleotide separations. Example 5 provides evidence of such as observed in the form of improved recoveries and more accurate profiling of a sample's composition, particularly with respect to the first chromatograms obtained with a column.

In this work, a mixture of 15 (SEQ ID NO: 2), 20 (SEQ ID NO: 3), 25 (SEQ ID NO: 4), 30 (SEQ ID NO: 5), 35 (SEQ ID NO: 6) and 40-mer (SEQ ID NO: 7) deoxythymidine was separated using columns constructed from a 1.7 μm organosilica 130 Å $C_{18}$ bonded stationary phase packed into either uncoated or vapor deposition coated hardware. Separations were performed with an Ultra High Performance Liquid Chromatography (UHPLC) system such as a system commercially available from Waters Corp. (Milford, MA) as an ACQUITY™ UPLC® H-Class Bio instrument according to the experimental conditions outlined below. FIGS. 8A-F and 9 present comparisons of these separations and their resulting data as obtained with columns constructed of varying coatings and materials.

LC Conditions
  Columns: 1.7 μm organosilica 130 Å $C_{18}$ bonded stationary phase in a 2.1×50 mm column dimension
  Sample: 15 (SEQ ID NO: 2), 20 (SEQ ID NO: 3), 25 (SEQ ID NO: 4), 30 (SEQ ID NO: 5), 35 (SEQ ID NO: 6) and 40-mer (SEQ ID NO: 7) deoxythymidine (0.5 pmol/μL)
  Column Temperature: 60° C.
  Flow Rate: 0.2 mL/min
  Mobile Phase A: 400 mM HFIP, 15 mM TEA in water
  Mobile Phase B: 400 mM HFIP, 15 mM TEA in methanol
  Gradient: 18 to 28% B in 5 min
  Injection volume: 10 μL
  UV Detection: 260 nm Non-specific binding of oligonucleotides within chromatographic systems negatively impacts the ability to detect and accurately quantify these molecules. The mechanism of non-specific binding is due to the interaction of the analyte with metallic surfaces in the flow path. The present disclosure relates to the use of a coating to reduce non-specific binding in chromatographic systems to improve performance, e.g., limit of detection, initial performance, peak shape, retention times, accurate quantitation, repeatability of analysis, speed to result, and linear dynamic range, for oligonucleotide bioanalysis.

Example 10: Oligonucleotide Ion Pair RPLC

Figure 10:
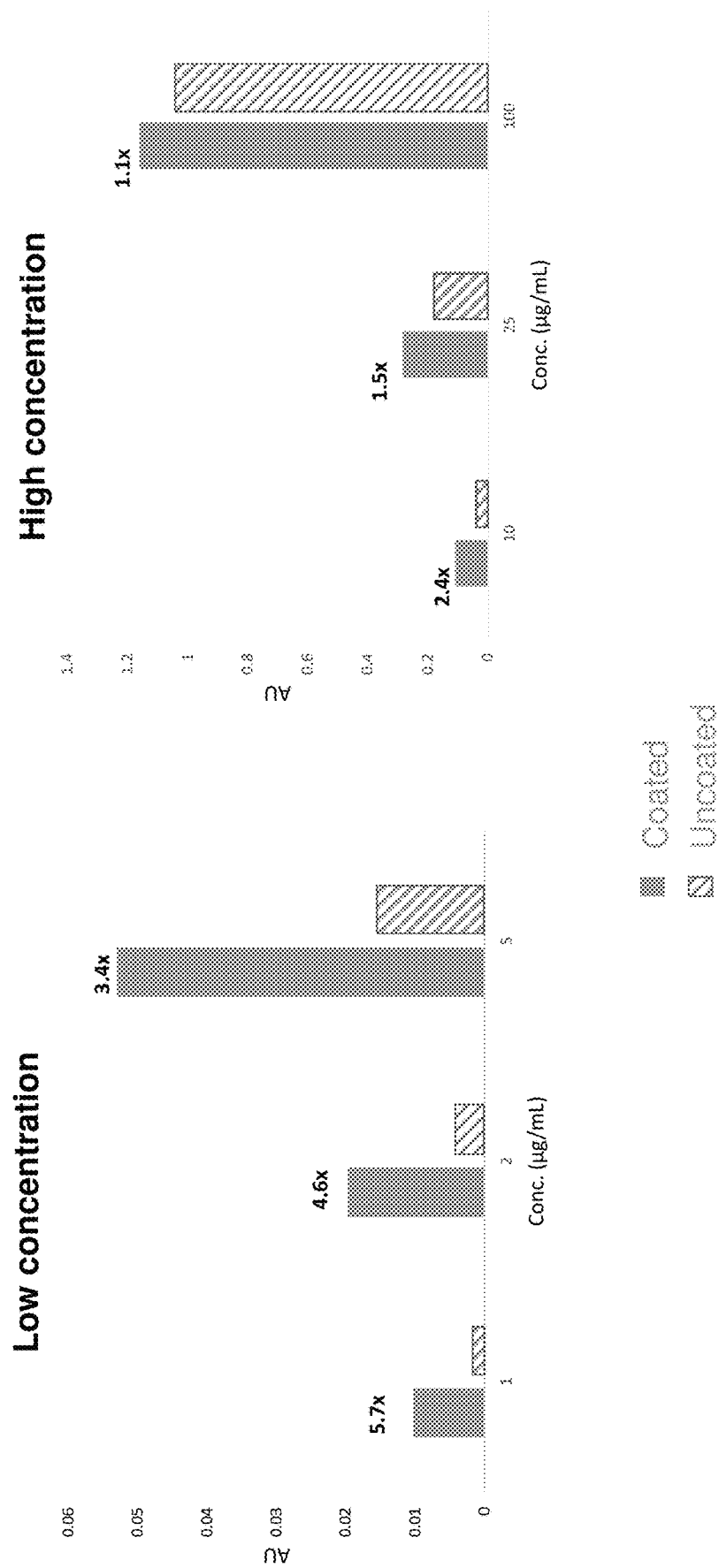
FIG. 10 is a graph showing the UV peak area from a range of concentrations of a 21mer ssRNA (5' rArUrG rGrArA rUrArC rUrCrU rUrGrG rUrUrA rCTT 3' (SEQ ID NO: 1)) injected onto either a 2.1×100 mm 1.7 µm organosilica 130 Å $C_{18}$ column constructed with untreated stainless steel (SS) or $C_2$ vapor deposition coated components, in accordance with an illustrative embodiment of the technology.

A standard curve of a 21mer ssRNA (5' rArUrG rGrArA rUrArC rUrCrU rUrGrG rUrUrA rCTT 3' (SEQ ID NO: 1)) was prepared in water at a concentration range of 1-100 μg/mL.
LC Conditions
  MPA: 10 mM TEAA
  MPB: 100 mM TEAA, 20% Acetonitrile pH 9.2
  Injection volume: 5 μL
  System: HClass Bio FTN
  Column temp: 30° C.
  UV detection at 260 nm
The results demonstrate (FIG. 10) that at low concentrations the area response is much larger for the coated system then it is for the uncoated system. This difference in response between coated and uncoated becomes less as the concentration of the analyte increases. For the example shown, at 1 μg/mL, the uncoated system is only able to recover 17% of the analyte that was injected onto the system.

Example 11: Oligonucleotide Separations

Interactions of analytes with metal surfaces in Ultra High Performance Liquid Chromatography (UHPLC) instruments and columns may cause a range of deleterious effects ranging from peak tailing to complete loss. These effects are due to interactions of certain analytes with the metal oxide layer on the surface of the metal components. A barrier technology has been applied to the metal surfaces in UHPLC instruments and columns to mitigate these interactions. A hybrid organic/inorganic barrier based on an ethylene-bridged siloxane structure was developed for use with reversed-phase and hydrophilic interaction chromatography. The performance of UHPLC instruments and columns that incorporate this barrier technology have been characterized and the results have been compared to those obtained using conventional instruments and columns. Improved performance has been shown when using the barrier technology for separations of an oligonucleotide. The barrier technology was found to result in improved analyte recovery and peak shape, particularly when using low analyte mass loads and acidic mobile phases. The results suggest that this technology will be particularly impactful in UHPLC/MS investigations of metal-sensitive analytes.

For the last fifty years, stainless steel has been the most commonly used construction material for HPLC instruments and columns. The combination of high strength, compatibility with a wide range of chemicals, manufacturability and low cost make it an excellent material for many applications.

However, stainless steel hardware can negatively impact the peak shape and recovery of some analytes. Analytes that show these effects typically contain functional groups such as phosphate and carboxylate groups that can form chelation complexes with iron and other transition metal ions. Stainless steel is susceptible to corrosion, particularly when exposed to acidic and/or halide-containing mobile phases, and corroded surfaces may be particularly prone to interacting with certain analytes. Alternative metals such as titanium and MP35N (a nickel-cobalt alloy) have been used for some applications because of their improved corrosion resistance, but still cause deleterious chromatographic effects for certain analytes. The engineering plastic polyether ether ketone (PEEK) has been employed to avoid these effects, but suffers from limited pressure resistance and some solvent incompatibilities. PEEK is also relatively hydrophobic and may require conditioning to avoid losses of hydrophobic analytes.

An alternative approach to mitigate interactions of analytes with metal surfaces is to add chelators such as ethylenediaminetetraacetic acid to the mobile phase or sample. Volatile chelators such as citric acid, acetylacetone and medronic acid have been used for LC/MS analyses. However, the use of chelators can negatively impact chromatographic selectivity and MS sensitivity. To address these issues, the use of a hybrid organic/inorganic barrier surface applied to the metal substrates in UHPLC instruments and columns was explored. A hybrid barrier surface based on an ethylene-bridged siloxane polymer has been found to be well-suited for reversed-phase (RP) and hydrophilic interaction chromatography (HILIC). Evaluations of the performance of UHPLC instruments and columns incorporating this hybrid barrier surface (HBS) technology relative to conventional instruments and columns were explored.

Reagents and Standards. Trecovirsen, a 25-mer phosphorothioate oligonucleotide with the sequence CTC TCG CAC CCA TCT CTC TCC TTC T (SEQ ID NO: 8), was acquired from Integrated DNA Technologies, Inc. (Coralville, IA). Undoped, polished, <100> orientation silicon wafers were obtained from Silicon Materials, Inc. (Pittsburgh, PA).

Instrumentation. A Model 190 CA Goniometer (available from ramé-hart instrument co., Succasunna, NJ) was used to measure contact angles on silicon wafers to which the hybrid barrier surface was applied.

Chromatographic Conditions—Oligonucleotide Separations. Trecovirsen was analyzed by LC-UV using UHPLC such as a system commercially available from Waters Corp. (Milford, MA) as HBS-modified ACQUITY™ UPLC® H-Class Bio System. Separations were performed on three sets of 1.7 μm BEH $C_{18}$ 2.1×50 mm stainless steel columns, using a mobile phase comprised of 15 mM triethylamine, 400 mM HFIP in water (mobile phase A) and a 50:50 (v/v) solution of mobile phase A and methanol (mobile phase B). Separations were also performed using columns of the same dimensions constructed with hardware modified with the HBS and packed with the same batch of stationary phase for comparison testing. Separations were run at a temperature of 60° C., a flow rate of 0.2 mL/min, and a gradient from 0.5-40% B in 12 min, followed by 40-80% B in 2 min. Samples were tested before and after conditioning the columns with 0.2 μg high mass load injections of trecovirsen. Prior to column conditioning, four injections of trecovirsen at a mass load of 1.5 ng were made. Next, the columns were conditioned by injecting 0.2 μg of trecovirsen followed by 10 μL of water to ensure no carryover of the oligonucleotide. This was followed by a fifth 1.5 ng mass load injection of trecovirsen to assess analyte recovery on the conditioned columns. Analyses were performed with UV detection at 260 nm using MassLynx™ 4.1 (available from Waters Corp., Milford, MA) for data acquisition and UNIFI 1.8 (available from Waters Corp., Milford, MA) for data analysis. A Xevo® TQ-XS mass spectrometer (available from Waters Corp., Milford, MA) was used for MS detection with a capillary voltage of 2.0 kV, sampling cone at 45, source offset at 30, a source temperature of 150° C., a desolvation temperature of 600° C., desolvation gas flow set at 1000 L/h, and a collision energy set at 5 eV.

Evaluation for Oligonucleotide Separations. The utility of UHPLC columns constructed with the HBS for the analysis of oligonucleotides was investigated. The analyte chosen for Example 11 was trecovirsen, a 25-mer antisense oligonucleotide phosphorothioate that has been studied as a treatment for HIV-1. The UHPLC system used for this experiment had components that were treated with the HBS. An ion-pairing mobile phase system containing 15 mM triethylamine (TEA), 400 mM HFIP and methanol was employed. The same lot of stationary phase was packed in both stainless steel columns and columns constructed using the HBS. Three columns of each type were evaluated. The initial performance from the first four injections of 1.5 ng of trecovirsen was evaluated before conditioning the columns with a high mass load (200 ng) of this oligonucleotide. A fifth injection was then made in order to determine whether conditioning gave any improvements in chromatographic performance.

Figures 11A, 11B:
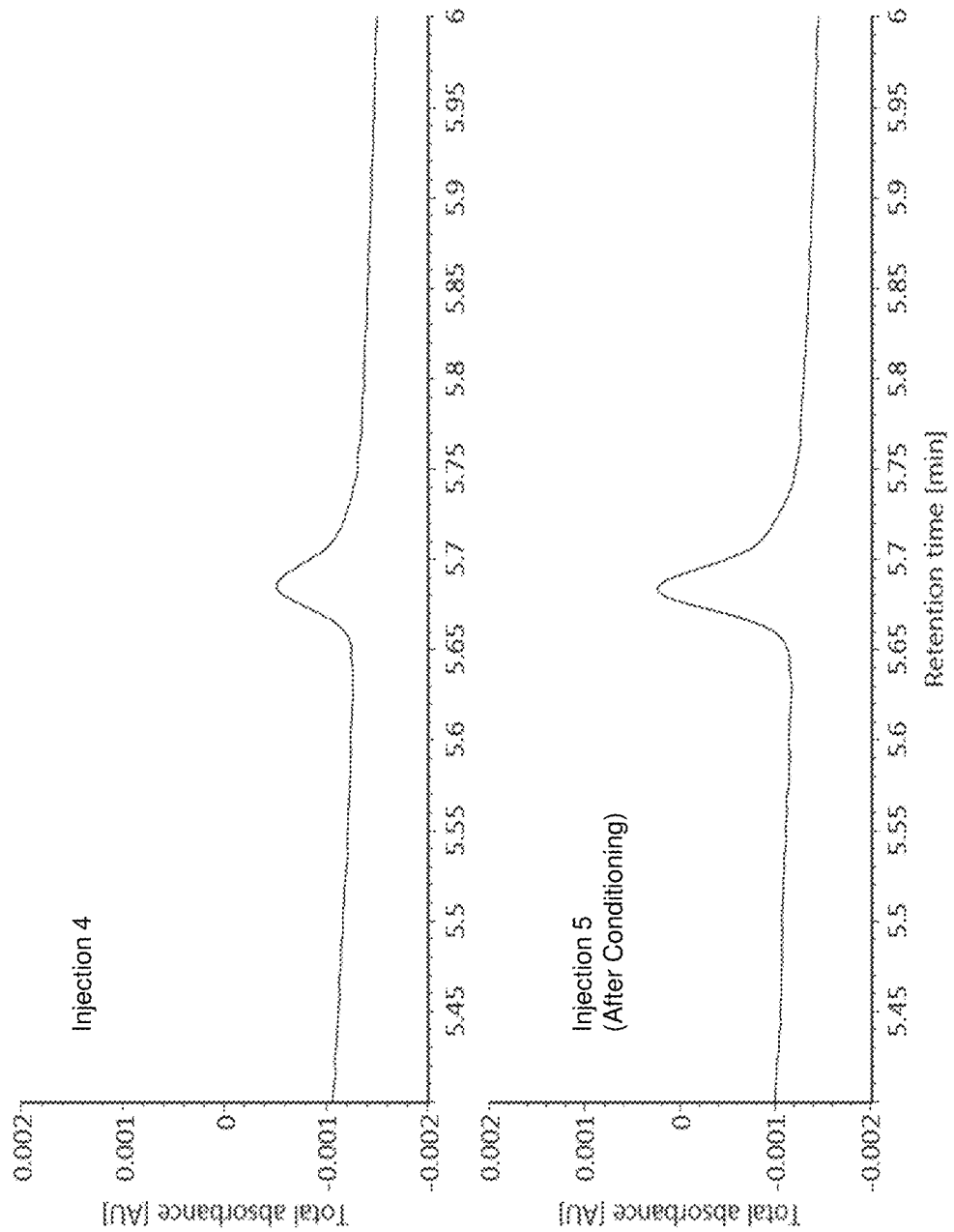
FIG. 11A is a display of a UV chromatogram of the fourth injection (before conditioning) of trecovirsen obtained using a standard column.
FIG. 11B is a display of a UV chromatogram of the fifth injection (after conditioning) of trecovirsen obtained using a standard column.
Figures 11C, 11D:
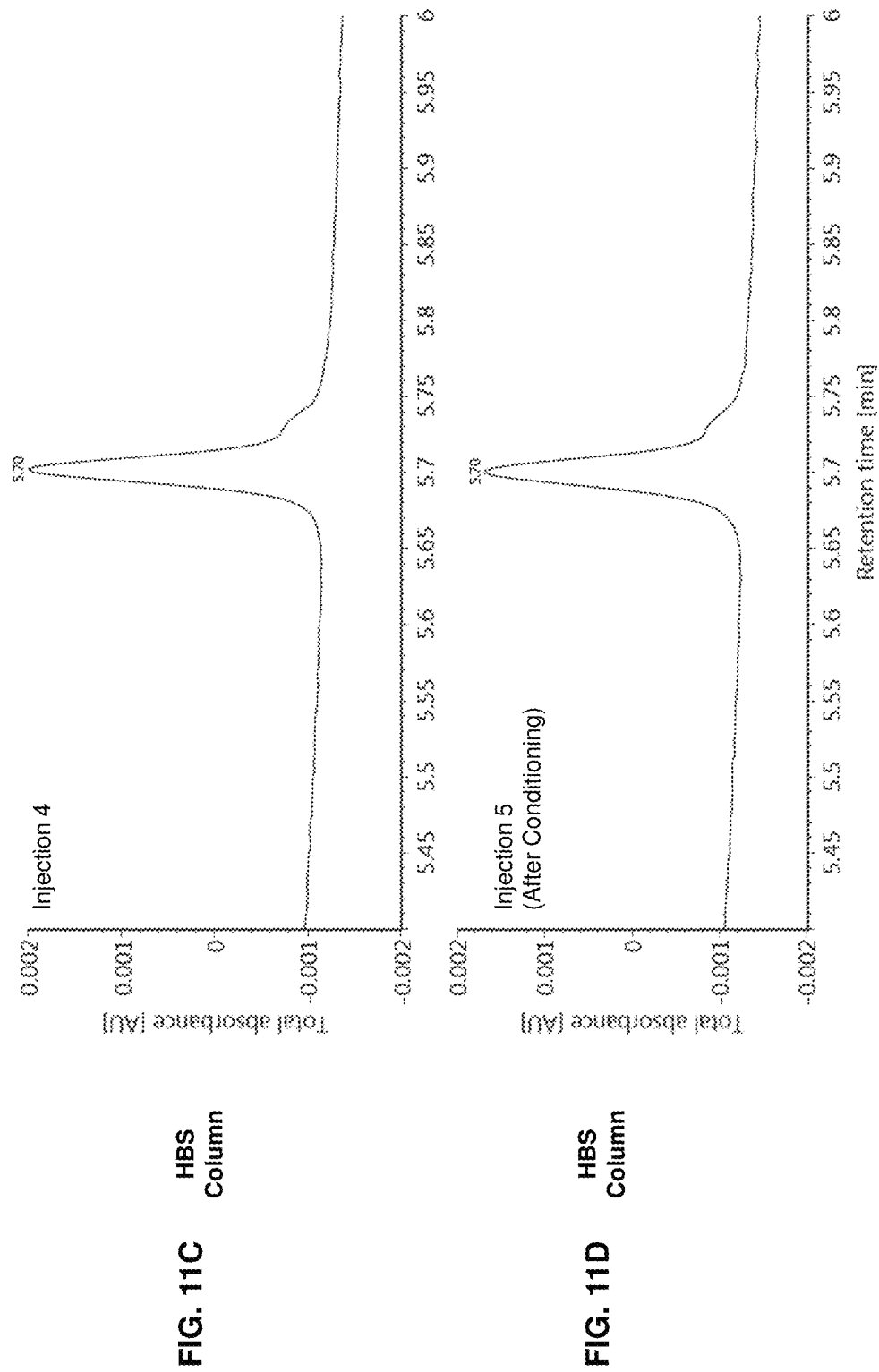
FIG. 11C is a display of UV chromatograms of the fourth injection (before conditioning) of trecovirsen obtained using a column constructed using HBS hardware, in accordance with an illustrative embodiment of the technology.
FIG. 11D is a display of UV chromatograms of the fifth injection (after conditioning) of trecovirsen obtained using a column constructed using HBS hardware, in accordance with an illustrative embodiment of the technology.

FIG. 11A is a display of a UV chromatogram of the fourth injection (before conditioning) of trecovirsen obtained using a standard column (2.1×50 mm). FIG. 11B is a display of a UV chromatogram of the fifth injection (after conditioning) of trecovirsen obtained using a standard column (2.1×50 mm). FIG. 11C is a display of UV chromatograms of the fourth injection (before conditioning) of trecovirsen obtained using a column constructed using HBS hardware (2.1×50 mm). FIG. 11D is a display of UV chromatograms of the fifth injection (after conditioning) of trecovirsen obtained using a column constructed using HBS hardware (2.1×50 mm). For FIG. 11E, separations were performed with an OST $C_{18}$ 130 Å, 1.7 μm stationary phase (available from Waters Corp., Milford, MA) using a flow rate of 0.2 mL/min, column temperature of 60° C., TEA-HFIP modified mobile phases, and 1.5 ng mass loads. The UHPLC system used for this experiment used parts that were treated with the HBS. Average peak areas of trecovirsen vs. injection number obtained using standard columns or columns constructed using HBS hardware (n=3). The error bars show ± one standard deviation for the three columns of each type.

Figure 11E:
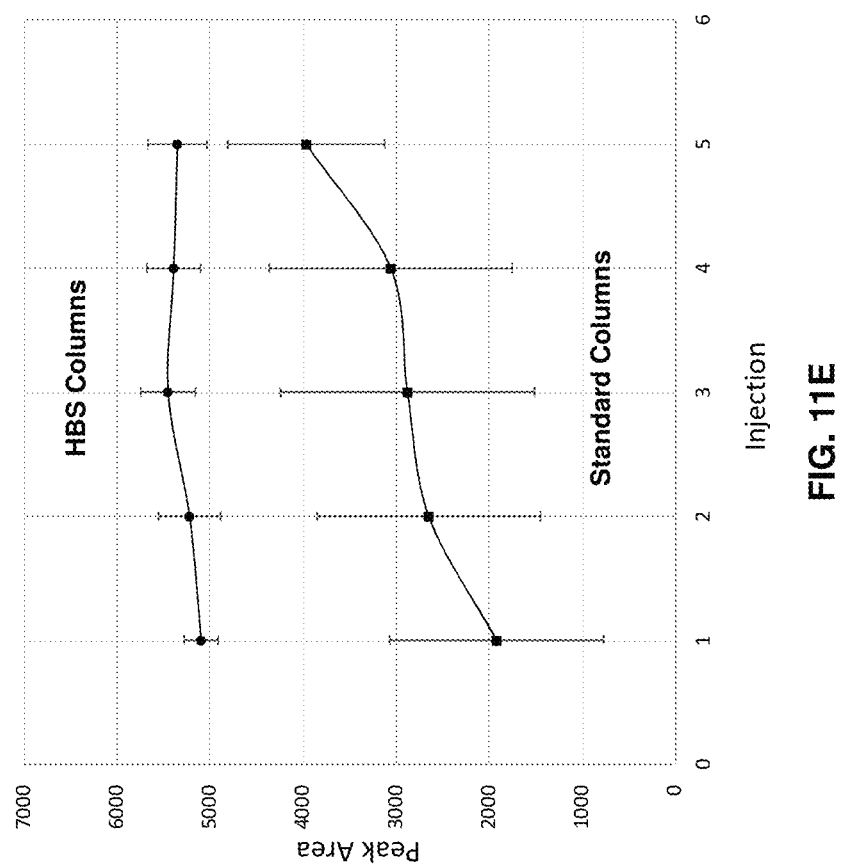
FIG. 11E is a display of separations performed with an OST $C_{18}$ 130 Å, 1.7 µm stationary phase using a flow rate of 0.2 mL/min, column temperature of 60° C., TEA-HFIP modified mobile phases, and 1.5 ng mass loads, in accordance with an illustrative embodiment of the technology.

Representative UV chromatograms resulting from the fourth and fifth injections are shown in FIGS. 11A-11D. For the first injections on the standard columns, the average peak area of trecovirsen was 2-3 fold lower than that obtained using the HBS columns (FIG. 11E). The relative standard deviations calculated from the results for the three standard columns were also greater by a factor of 8-17, as shown by the size of the ± one standard deviation error bars in FIG. 11E. Moreover, peak widths were decreased by 30% using the HBS columns. After conditioning, the peak areas and peak widths improved by 30% and 6%, respectively, for columns packed in standard column hardware. Columns constructed with the HBS showed reproducible performance over the five injections regardless of column conditioning (FIG. 11E). Post-conditioning changes in average peak area and peak width were less than 1% when using the HBS columns. Even after conditioning the standard stainless steel columns, the peak area of trecovirsen was still only 74% of the peak area from the HBS columns.

Further differences in the chromatography were noticed in the resolution of co-eluting, lower abundant oligonucleotide species, as shown in FIGS. 11A-11D. A later eluting peak which was obscured by the main peak when using standard columns could be partially resolved when using the HBS columns. Through mass spectrometric analysis performed with electrospray ionization and a tandem quadrupole mass spectrometer, this peak was identified as a +53 Da impurity of the main peak. This impurity is likely a cyanoethylation of the oligonucleotide, which typically occurs on thymidines during the synthesis process.

The HBS technology described here provides a means to improve UHPLC analyses of analytes that interact with metal surfaces. High recoveries and more symmetric peaks have been demonstrated to be obtainable using UHPLC systems and columns that incorporate this technology, even for challenging analytes such as a phosphorothioated oligonucleotide. In addition, significant benefits have been observed for analytes containing multiple carboxylate groups, such as citric acid and acidic peptides.

HBS UHPLC systems and columns have been shown to give the biggest improvement over their standard counterparts at low mass loads. This suggests that methods employing UHPLC/MS will benefit greatly from this technology, particularly when trace level quantitative measurements are needed. Work is in progress to further demonstrate the range of applications that benefit from this technology.

---

What is claimed is:

1. A method of separating a sample comprising a low concentration of analyte:
    providing a chromatographic system having a layer of alkylsilyl on at least a portion of a metallic flow path;
    injecting the sample into the alkylsilyl coated metallic flow path of the chromatographic system;
    flowing the sample through the alkylsilyl coated metallic flow path of the chromatographic system;
    separating the sample;
    detecting at least an amount of the low concentration of the analyte above a minimum expected value; and recovering greater than 80 percent of the analyte when the low concentration of the analyte extends from about 1 ng/mL to about 5 μg/mL.

2. The method of claim 1, wherein injecting the sample is a first injection, and
    wherein detecting comprises detecting the low concentration of the analyte after the first injection when the low concentration of the analyte extends from about 1 ng/mL to about 5 μg/mL.

3. The method of claim 1, wherein the layer of alkylsilyl increases recovery of the analyte with the concentration of the analyte extending from about 1 ng/mL to about 5 μg/mL.

4. The method of claim 1, wherein the layer of alkylsilyl decreases a minimum concentration of a linear dynamic range of the chromatographic system.

5. The method of claim 1, wherein the layer of alkylsilyl increases a linear dynamic range of the chromatographic system.

6. The method of claim 1, wherein a linear dynamic range of the chromatographic system with the layer of alkylsilyl is greater than a chromatographic system without an alkylsilyl coating.

7. The method of claim 1, wherein a minimum of a linear dynamic range of the chromatographic system remains substantially similar over the first 50 injections.

8. The method of claim 1, wherein a chromatographic peak shape of the analyte of the separated sample is substantially similar to a reference chromatographic peak shape.

9. The method of claim 1, wherein the layer of alkylsilyl increases the similarity between a chromatographic peak shape of the analyte of the separated sample and a reference chromatographic peak shape.

10. The method of claim 1, wherein the layer of alkylsilyl is uniformly distributed, such that column walls defining the flow path are entirely coated.

11. The method of claim 1, wherein the layer of alkylsilyl on the walls of the flow path has a thickness of about 100 Å to about 1600 Å.

12. The method of claim 1, further comprising injecting another 50 samples,
wherein a concentration of the analyte of the 50 samples is substantially similar to the low concentration of the analyte of the first sample, and
wherein the percent recovered of the analyte is substantially similar for all the samples.

13. The method of claim 1, further comprising injecting another 50 samples,
wherein a concentration of the analyte of the 50 samples is substantially similar to the concentration of the analyte of the first sample, and
wherein an accuracy of the analyte detected is substantially similar for all the analyte samples.

14. A method of separating a sample comprising:
flowing a first sample comprising oligonucleotides through a system having a fluid-contacting coating on metallic surfaces defining a flow path, wherein the coating comprises an alkylsilyl;
separating the first sample;
detecting an analyte in the first sample;
washing the flow path;
flowing a second sample comprising oligonucleotides through the system;
separating the second sample; and
detecting the second sample, wherein a detected signal from the second sample is within 5% of a detected signal from the first sample and is within 10% of an expected value.

15. The method of claim 14, wherein flowing the second sample is immediately preceded by washing the flow path.

16. The method of claim 14, wherein separating the first sample and the second sample produce a substantially similar analyte signal.

17. The method of claim 14, wherein the system is a chromatographic system.

18. The method of claim 1, wherein the layer of alkylsilyl comprises bis(trichlorosilyl)ethane or bis(trimethoxysilyl)ethane.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
auggaauacu cuugguuact t                                                   21

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tttttttttt ttttt                                                          15

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tttttttttt tttttttttt                                                     20

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tttttttttt tttttttttt ttttt                                               25

<210> SEQ ID NO 5
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tttttttttt tttttttttt tttttttttt                                    30

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tttttttttt tttttttttt tttttttttt ttttt                              35

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tttttttttt tttttttttt tttttttttt tttttttttt                         40

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ctctcgcacc catctctctc cttct                                         25
```